(12) United States Patent
Björk et al.

(10) Patent No.: US 10,159,806 B2
(45) Date of Patent: *Dec. 25, 2018

(54) MEDICAMENT DELIVERY DEVICE

(71) Applicant: CAREBAY EUROPE LTD, Valleta (MT)

(72) Inventors: Emil Björk, Stockholm (SE); Stephan Olson, Danderyd (SE); Jochen Ratjen, Nacka (SE); Gunnar Elmén, Huddinge (SE)

(73) Assignee: CAREBAY EUROPE LTD, Sliema (MT)

( * ) Notice: Subject to any disclaimer, the term of this patent is extended or adjusted under 35 U.S.C. 154(b) by 103 days.

This patent is subject to a terminal disclaimer.

(21) Appl. No.: 15/419,122

(22) Filed: Jan. 30, 2017

(65) Prior Publication Data
US 2017/0165433 A1    Jun. 15, 2017

Related U.S. Application Data

(63) Continuation of application No. 14/384,757, filed as application No. PCT/EP2013/054654 on Mar. 7, 2013, now Pat. No. 9,592,351.
(Continued)

(30) Foreign Application Priority Data

Mar. 14, 2012    (SE) ........................ 1250238
Nov. 1, 2012    (SE) ........................ 1251235

(51) Int. Cl.
*A61M 5/32*    (2006.01)
*A61M 15/00*    (2006.01)
*A61M 5/20*    (2006.01)
*A61M 5/24*    (2006.01)

(52) U.S. Cl.
CPC ............ *A61M 5/3287* (2013.01); *A61M 5/20* (2013.01); *A61M 5/24* (2013.01); *A61M 5/3202* (2013.01);
(Continued)

(58) Field of Classification Search
CPC .... A61M 5/3287; A61M 5/24; A61M 5/3202; A61M 5/3243; A61M 5/3204
See application file for complete search history.

(56) References Cited

U.S. PATENT DOCUMENTS

2004/0010234 A1    1/2004  Hung et al.
2007/0135767 A1    6/2007  Gillespie et al.
(Continued)

FOREIGN PATENT DOCUMENTS

GB    2451663    2/2009
GB    2471473    1/2011
(Continued)

OTHER PUBLICATIONS

International Search Report for Int. App. No. PCT/EP2013/054654, completed Sep. 3, 2013.

*Primary Examiner* — Bradley J Osinski
(74) *Attorney, Agent, or Firm* — McDonnell Boehnen Hulbert & Berghoff LLP

(57) ABSTRACT

A medicament delivery device is presented having a housing configured to receive a medicament container having a delivery member and a shield, a protective cap, and wherein the protective cap comprises connecting means for connecting to the shield of the medicament container such that removal of the protective cap from the housing causes removal of the shield from the medicament container. The delivery device is characterized in that a protective cap assembly has a first disconnecting means configured to interact with corresponding second disconnecting means of
(Continued)

the housing and of the protective cap such that activation of the first disconnecting means of the protective cap assembly causes the displacement of the protective cap relative to the housing.

10 Claims, 34 Drawing Sheets

Related U.S. Application Data

(60) Provisional application No. 61/610,567, filed on Mar. 14, 2012, provisional application No. 61/721,049, filed on Nov. 1, 2012.

(52) U.S. Cl.
CPC ........ *A61M 5/3204* (2013.01); *A61M 5/3243* (2013.01); *A61M 15/0021* (2014.02)

(56) References Cited

U.S. PATENT DOCUMENTS

| | | |
|---|---|---|
| 2008/0021397 A1 | 1/2008 | Kirchhofer et al. |
| 2010/0016793 A1 | 1/2010 | Jennings et al. |
| 2012/0186075 A1 | 7/2012 | Edginton |
| 2014/0025013 A1 | 1/2014 | Dowds et al. |

FOREIGN PATENT DOCUMENTS

| | | |
|---|---|---|
| WO | 00/24441 | 5/2000 |
| WO | 2005/115508 | 12/2005 |
| WO | 2006/106290 | 10/2006 |
| WO | 2007/047200 | 4/2007 |
| WO | 2008/086004 | 7/2008 |
| WO | 2009/019440 | 2/2009 |
| WO | 2011/012903 | 2/2011 |
| WO | 2011/076281 | 6/2011 |

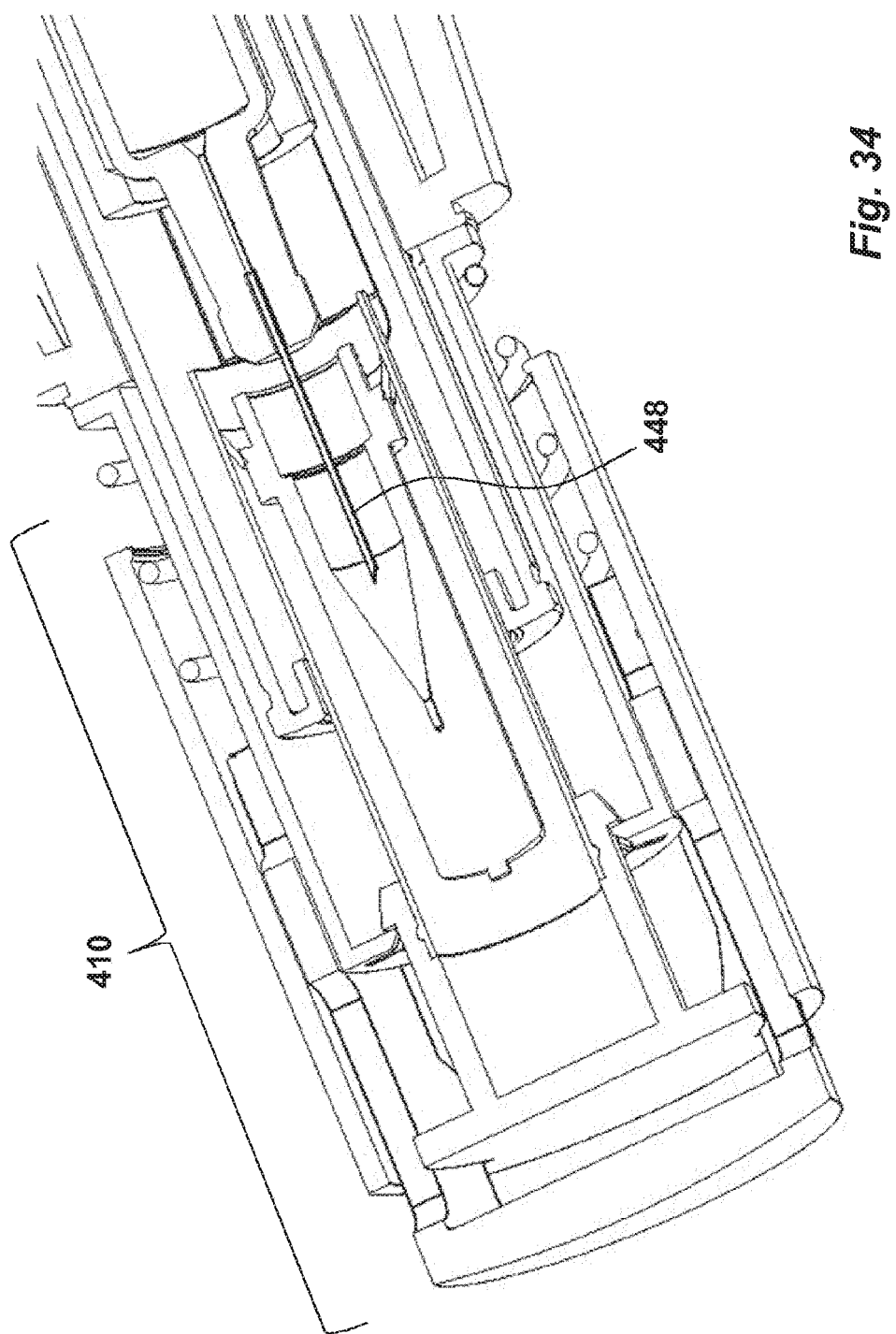

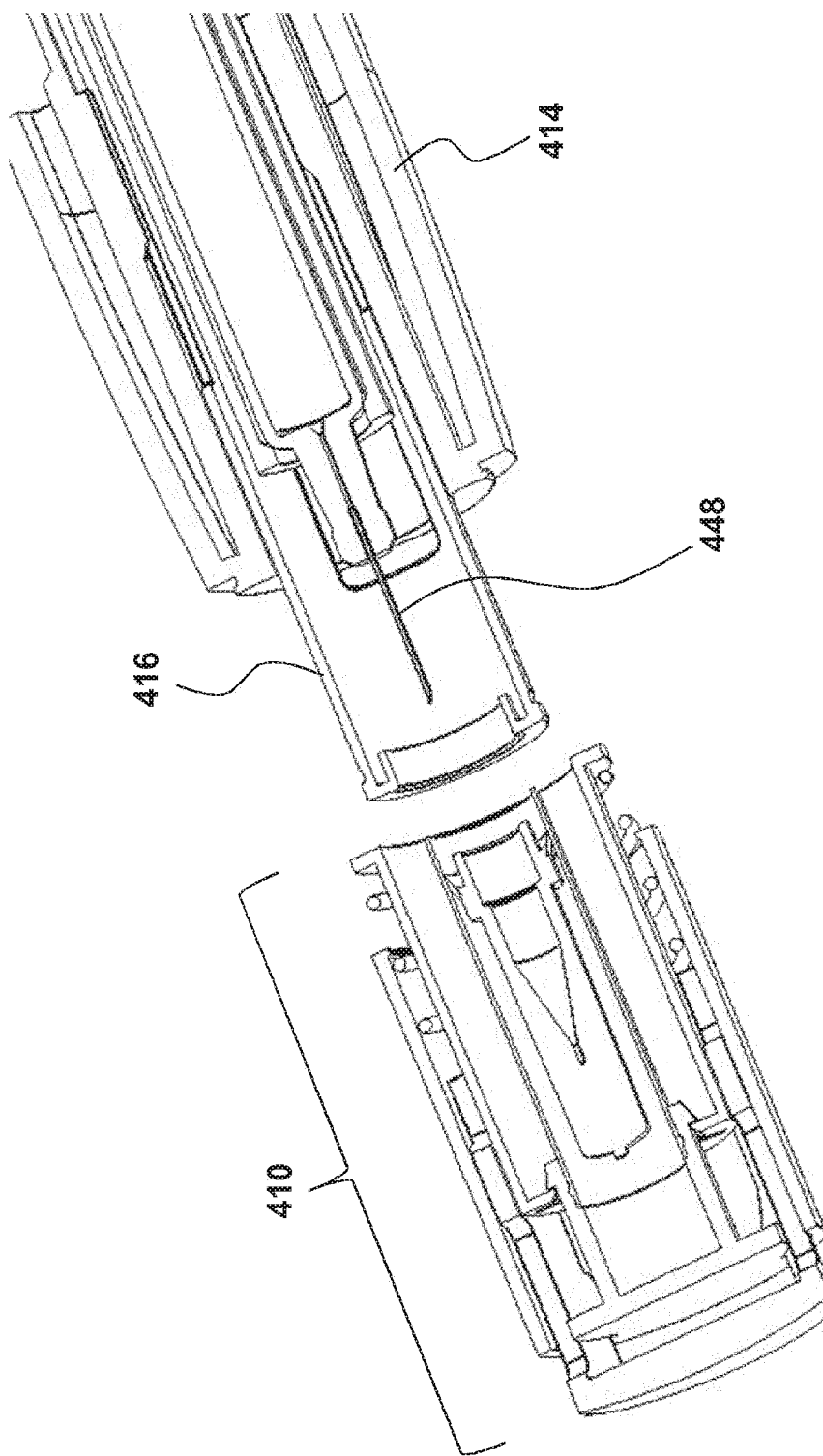

MEDICAMENT DELIVERY DEVICE

CROSS REFERENCE TO RELATED APPLICATIONS

The present application is a continuation of U.S. patent application Ser. No. 14/384,757, filed Sep. 12, 2014, which is a U.S. National Phase Application pursuant to 35 U.S.C. § 371 of International Application No. PCT/EP2013/054654 filed Mar. 7, 2013, which claims priority to Swedish Patent Application No. 1250238-1 filed Mar. 14, 2012, which is claims priority to U.S. Provisional Patent Application No. 61/610,567, filed Mar. 14, 2012. The present application also claims priority to Swedish Patent Application No. 1251235-6 filed Nov. 1, 2012 which claims priority to U.S. Provisional Patent Application No. 61/721,049, filed Nov. 1, 2012. The entire disclosure contents of these applications are herewith incorporated by reference into the present application.

TECHNICAL AREA

The present invention relates to a medicament delivery device arranged with a protective cap assembly designed for removal of needle shields off medicament containers of the medicament delivery device.

BACKGROUND

There are many medicament delivery devices on the market that have been developed for self administration of medicament, where one large group is medicament injection devices. Many of these injection devices have been provided with removable needle cover assemblies where the core cover may be a so called Rigid Needle Cover or Rigid Needle Shield (RNS) or a so called Flexible Needle Cover or Flexible Needle Shield (FNS).

These RNS/FNS's are arranged to protect the injection needle before use in order to keep the needle sterile and also protect from unintentional needle sticks. Many of these RNS/FNS's are pushed onto the neck portion of a medicament container, such as a syringe, where the RNS/FNS are provided with an inner cap in contact with the surface of the syringe. The inner cap is preferably of a resilient material, normally rubber that ensures a tight grip and a good seal between the cap and the syringe. However this tight grip entail problem in that it is difficult to remove the RNS/FNS from the syringe in order to perform an injection.

Therefore a number of RNS/FNS removal devices have been developed, which are intended to aid the user in removing the RNS. Documents WO2007/047200, WO 2006/106290 and WO 2005/115508 disclose different solutions to this problem. However, they all include a function where the whole assembly including the RNS and its resilient inner cap, are twisted or rotated manually. This a major drawback since this twisting action if the inner cap very easily causes damage to the injection needles, which usually are thin and easily bendable such that when the RNS is removed, the needle has become so damaged it cannot be used for the injection.

Also, all these solutions require manual action by gripping the shield remover mechanism and performing a number of manual operations such as twisting and pulling and combinations thereof. This is a drawback for all persons with reduced dexterity in their hands as well as reduced motion control. Further, all these solutions require change of grip of the medicament delivery device after removal of the RNS/FNS. This may also be a drawback in that the injection needle now is exposed when the user is to change grip for the subsequent penetration and injection. Not only may the thin needle be damaged during the process, but the user or other persons in the vicinity may be damaged by the exposed needle.

Document WO 2009/019440 discloses an injection device comprising a cap that in order to be removed is rotated turns about the longitudinal axis. During rotation, the needle shield retainer does not rotate relative to a discharge nozzle and the rotational movement of the cap relative to the housing is converted into linear movement of the needle shield retainer away from the exit aperture in the axial direction achieved through engagement of the screw threads so the needle shield is pulled away from the discharge nozzle through the exit aperture into the central boss. After rotation, the user finally pulls the cap away from the housing, the needle shield and the discharge nozzle are not engaged with each other and the cap becomes completely detached from the injection device.

The device according to '440 does not thus twist or rotate the needle shield but a rotational interaction with threaded components causes a linear movement of the needle shield retainer from the exit aperture of the medicament delivery device. However, the solution is complex regarding the number of components required, and still a manual gripping action as described above is required. Again, the user has to change grip after removal of the needle shield with the addressed risks that this may induce.

There is thus a need for solutions that simplify the removal of needle shields from medicament delivery devices, reducing the risk of damaging the needle as well as reducing the risk of injuring persons.

SUMMARY

In the present application, when the term "distal" is used, this refers to the direction pointing away from the close delivery site. When the term "distal part/end" is used, this refers to the part/end of the delivery device, or the parts/ends of the members thereof, which is/are located furthest away from the close delivery site. Correspondingly, when the term "proximal" is used, this refers to the direction pointing to the close delivery site. When the term "proximal part/end" is used, this refers to the part/end of the delivery device, or the parts/ends of the members thereof, which is/are located closest to the close delivery site.

According to a main aspect of the invention, it is characterised by the features of the independent patent claim 1. Preferable embodiments of the present invention form the subject of the dependent patent claims.

The present invention relates to a medicament delivery device. Preferably the medicament deliver device may comprise a housing with at least one housing part, which is configured to receive a medicament container.

The medicament container is provided with a delivery member, either integral with the medicament container, or arranged as an attachable member. The medicament delivery member is further preferably arranged with a shield that covers said delivery member. In this respect it is to be understood that a number of different medicament delivery member shields are incorporated in the present invention, such as Rigid Needle Shields (RNS), Flexible Needle Shields (FNS) and combinations of these are just a few of the feasible shields.

The housing may comprise first connecting means, wherein the device further may comprise a protective cap assembly comprising a protective cap, which cap may comprise second connecting means. The first and the second connecting means are configured such that a displacement of the protective cap relative to the housing allows the protective cap to be removed from the housing. In this respect it is to be understood that the displacement of the protective cap relative the housing may be a linear displacement, a rotational displacement as well as combinations of these.

Further, the first and second connecting means may be configured to achieve a positive connection. That is, the two connecting means are designed to lock with each other by the form of the connecting means. For example they may be configured as a bayonet connection or a threaded connection.

As an alternative, the first and second connecting means may be configured to achieve a non-positive connection. That is, the two connecting means are designed to lock with each other by friction between them.

Further, according to the present invention, the protective cap further comprises third connecting means for connecting to the shield of the medicament container such that removal of the protective cap from the housing causes removal of the shield from the medicament container.

According to one major feature of the invention, the protective cap assembly may further comprise first disconnecting means configured to interact with corresponding second disconnecting means of the housing and of the protective cap such that activation of the disconnecting means of the protective cap assembly causes the displacement of the protective cap relative to the housing. Again, it is to be understood that the displacement of the protective cap relative the housing may be a linear displacement, a rotational displacement as well as combinations of these.

According to one positive alternative of the present invention, the protective cap assembly may comprise an energy accumulating member. This energy accumulating member may be in the form of a mechanical spring member made of a number of materials that display the appropriate features. If a coiled spring is utilized, it may be a compression spring, a torsion spring, a flat clock spring, just to mention a few. Other feasible energy accumulating members may include plate springs, gas springs, resilient materials, and the like.

In order to handle the energy accumulating member, it is an advantage if the protective cap assembly also comprises an actuating mechanism configured to hold said energy accumulating member in an energized state, and configured, upon activation, to release said energy accumulating member for activation of said disconnecting means. With the actuating mechanism, it is for example possible to assemble the protective cap assembly before it is mounted onto the medicament delivery device.

The disconnecting means may comprises a number of different designs, where one possible design is to utilize a nut operably connected to said housing and to said protective cap and drivably connected to said energy accumulating member such that activation of said actuating mechanism causes said nut to displace said protective cap. If a nut is included in the protective cap assembly, it is an advantage if the energy accumulating member is capable of providing a rotating displacement as well as a displacement in the proximal direction. In this case, a torsion spring or a flat clock spring may be advantageous.

The mechanical connection between the nut and the housing said nut may have different designs. For example the nut may be arranged with threads arranged to cooperate with corresponding threads on said housing. According to another design, the nut may be arranged with a bayonet connection member arranged to cooperate with corresponding bayonet connection member on said housing.

According to another major aspect of the present invention, the protective cap assembly may comprise an actuator operatively connected to said housing and drivably connected to said energy accumulating member, and wherein said actuating mechanism is capable of holding said energy accumulating member by said actuator, such that release of said actuator causes activation of said disconnecting means.

With this design, the energy accumulating member may preferably comprise a compression spring operably arranged between said protective cap and said activator, thereby providing a linearly directed force in the proximal direction of the device.

In combination with the energy accumulating member, the actuating mechanism may comprise a button operably arranged on said protective cap. A button is easily managed by a user when positioned on the feature that is to be removed from the medicament delivery device before use.

The advantage with the above design is that the user does not require a lot of force or power in order to remove the protective cap. Once the energy accumulating member has been activated, the protective cap will automatically be removed from the device, after which the medicament delivery device is ready for medicament delivery. Further, because of the automatic function of removing the protective cap, the medicament delivery device can be designed such that the user does not need to change grip after removal.

According to a further major aspect of the invention, the disconnecting means my as an alternative or variant comprise a mechanical actuator arranged manually operable, such that a force applied on said actuator causes displacement of the protective cap relative to the housing. With this feature, the force of displacing the protective cap is obtained by other means than an energy accumulating means, whereby the force may be provided by a user holding the device with one grip.

For example the mechanical actuator is arranged to be operable by a force applied in the distal direction of the device. This means that the medicament delivery device may be pressed against a surface with its proximal end, which will provide a force in the distal direction. Further in this respect, the grip that the user is using for pressing the device against a surface for removing the protective cap, may well be the same grip used for the subsequent medicament delivery steps.

In order to further facilitate the removal of the protective cap, said disconnecting means may further comprise transmission means capable of transmitting a distally directed displacement of said mechanical actuator to a proximally directed displacement of said protective cap.

The transmission means may for example comprises a rotator operably connected to said mechanical actuator to rotate said rotator. In this respect it may be advantageous when the rotator is arranged with cam surfaces and protrusions and that said transmission means further comprises a guide member arranged with cam surfaces such that rotation of said rotator by said actuator causes a displacement of said rotator in the proximal direction of the device. The use of a rotator is positive in the sense that it is capable of providing several features and functions in one component. Nevertheless, the transmission means may instead comprise a leverage mechanism or other mechanical functions.

A further advantage with the use of a transmission means is that it may be designed to provide a protective cap displacement force that is larger than the actuator displacement force. Therefore, a user may not need to use so much force when pressing the device against a surface, which is an advantage for weak users or users with impaired functions of the hands.

According to a favourable embodiment of the present invention, the connecting means is a FNS/RNS remover, and in this respect the remover is operably arranged to said protective cap such that displacement of said protective cap causes an axial displacement of said remover and shield in relation to said medicament container.

In all a very versatile, user-friendly as well as safety-increasing device is obtained with the present invention.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION

Figure 1:
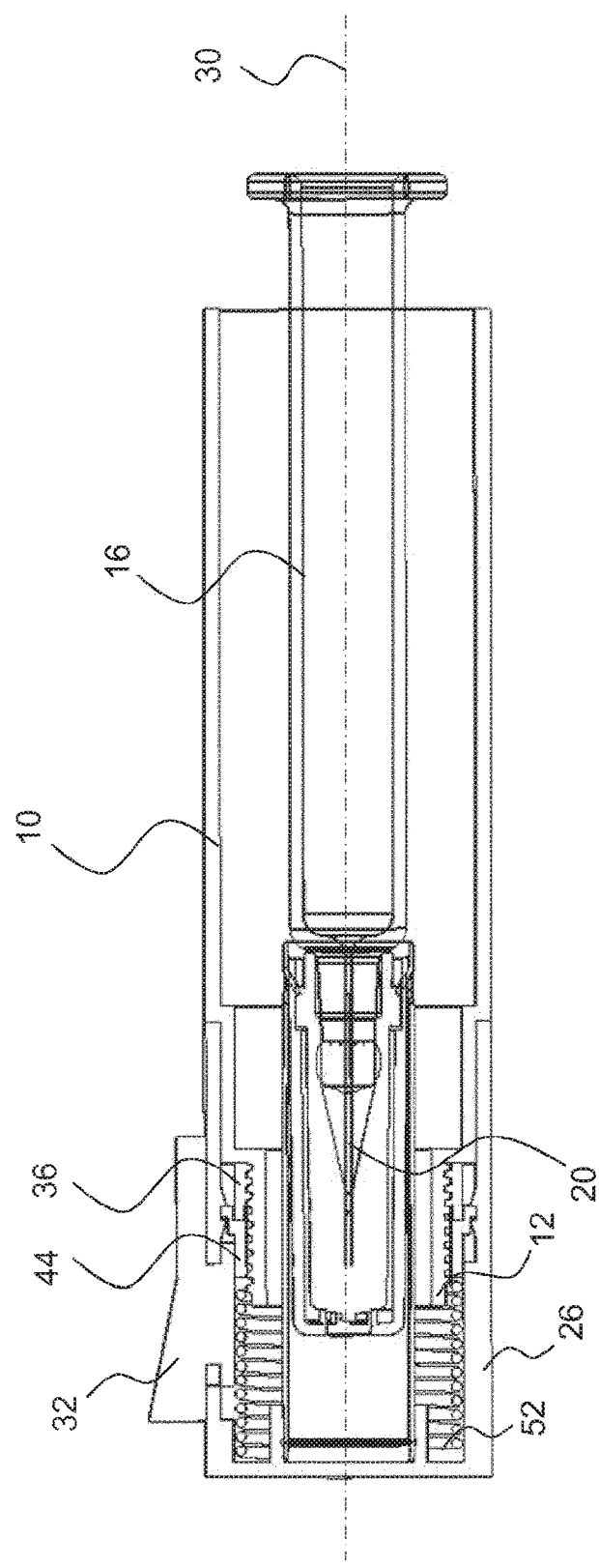
FIG. 1 is a cross-sectional view of a first embodiment of the present invention.

A first embodiment of the present invention is shown in the drawings 1 to 6. It comprises a proximal part, in the following named front shell 10. The front shell 10 is a part of a major housing where the rest of the housing has been removed for clarity. Other components and functions comprised in the device not part of the present invention have also been removed for clarity.

Figure 2:
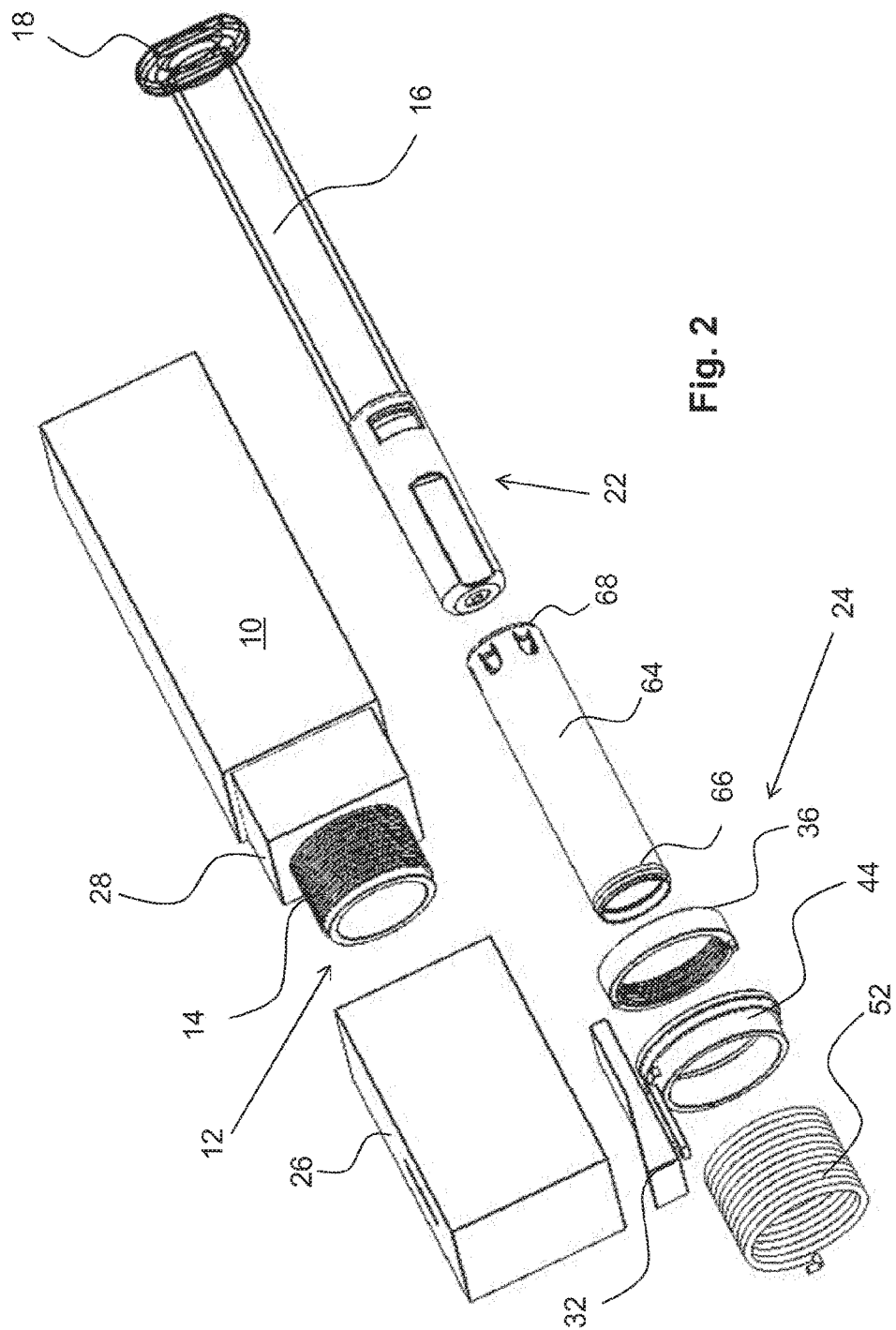
FIG. 2 is an exploded view of the embodiment of FIG. 1, FIGS. 3-6 are detailed views of components comprised in the embodiment of FIG. 1.
Figure 3:
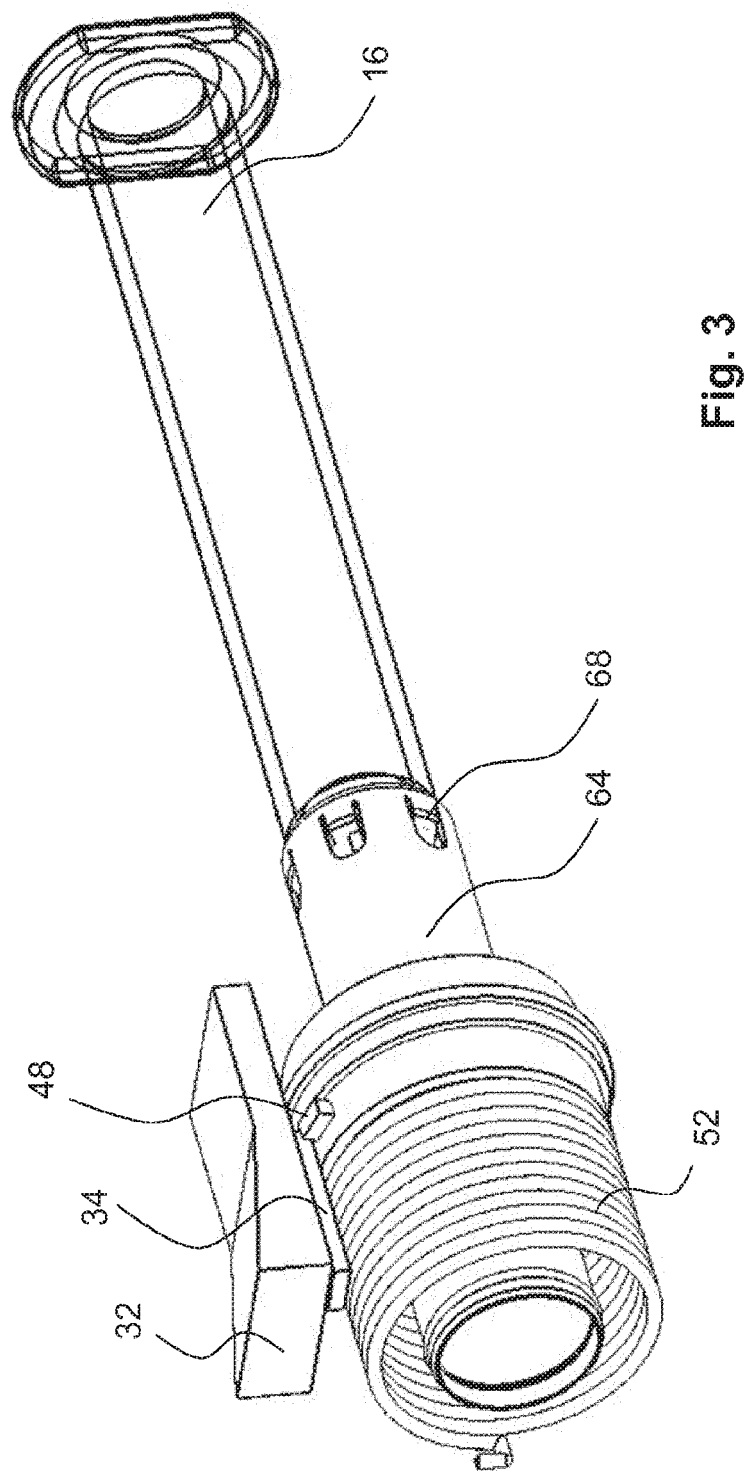

The front shell 10 is arranged with a proximally directed neck portion 12, FIG. 2, which neck portion 12 is arranged with threads 14 on its outer surface, which threads 14 form second disconnecting means of the housing. The front shell 10 is further arranged to accommodate a medicament container 16 in the form of an elongated cylindrical body with a collar 18 at its distal end. The inner space of the medicament container is filled with a medicament where its distal opening is closed by a movable stopper (not shown).

The proximal end of the medicament container 16 is arranged with a medicament delivery member, in the embodiment shown an injection needle 20. For protection, the injection needle is surrounded by a needle shield 22, FIG. 2, in the embodiment a so called RNS, rigid needle shield, which comprises an inner tubular sheath of elastic material, such as rubber, enclosing the injection needle. The RNS further comprises an outer shell of rigid material, which is enclosing and is attached to the sheath. The medicament container 16 with its RNS 22 is positioned in the front shell 10 such that the RNS 22 protrudes through the threaded proximal neck 12 of the front shell 10.

The device according to the present invention comprises a protective cap assembly 24, FIG. 2, that in the embodiment disclosed comprises a protective cap 26 having a distally directed opening 27, which forms second connecting means of the device. The protective cap and the front shell are designed such that the distal end of the protective cap 24 with its opening 27 can fit onto a recessed portion 28 of the front shell 10, which recessed portion 28 forms first connecting means of the device, with a certain friction between the two in a longitudinal direction 30 of the device, whereby the protective cap 26 and the front shell 10 are designed such that a rotational lock is obtained between the two.

Figure 6:
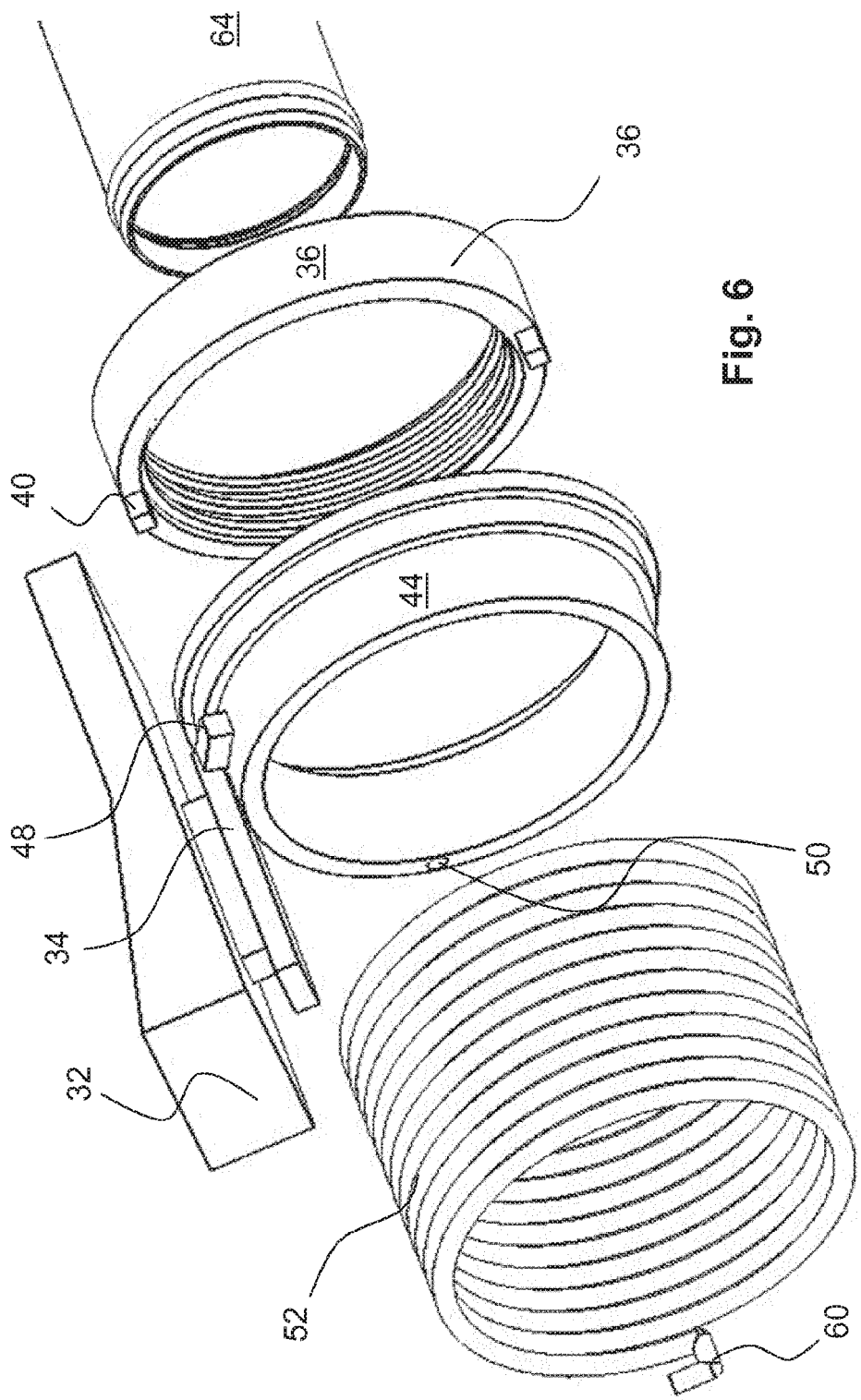

The protective cap assembly 24 further comprises an actuating mechanism including an activation member 32, in the embodiment shown in the form of a button 32, FIG. 6, which is slidably arranged on the outer surface of the protective cap 26. A portion of the button 32 extends into the protective cap via an opening, which portion of the button 32 is arranged with a plate-shaped actuation member 34, comprised in the actuating mechanism, and extending in the distal direction.

Figure 5:
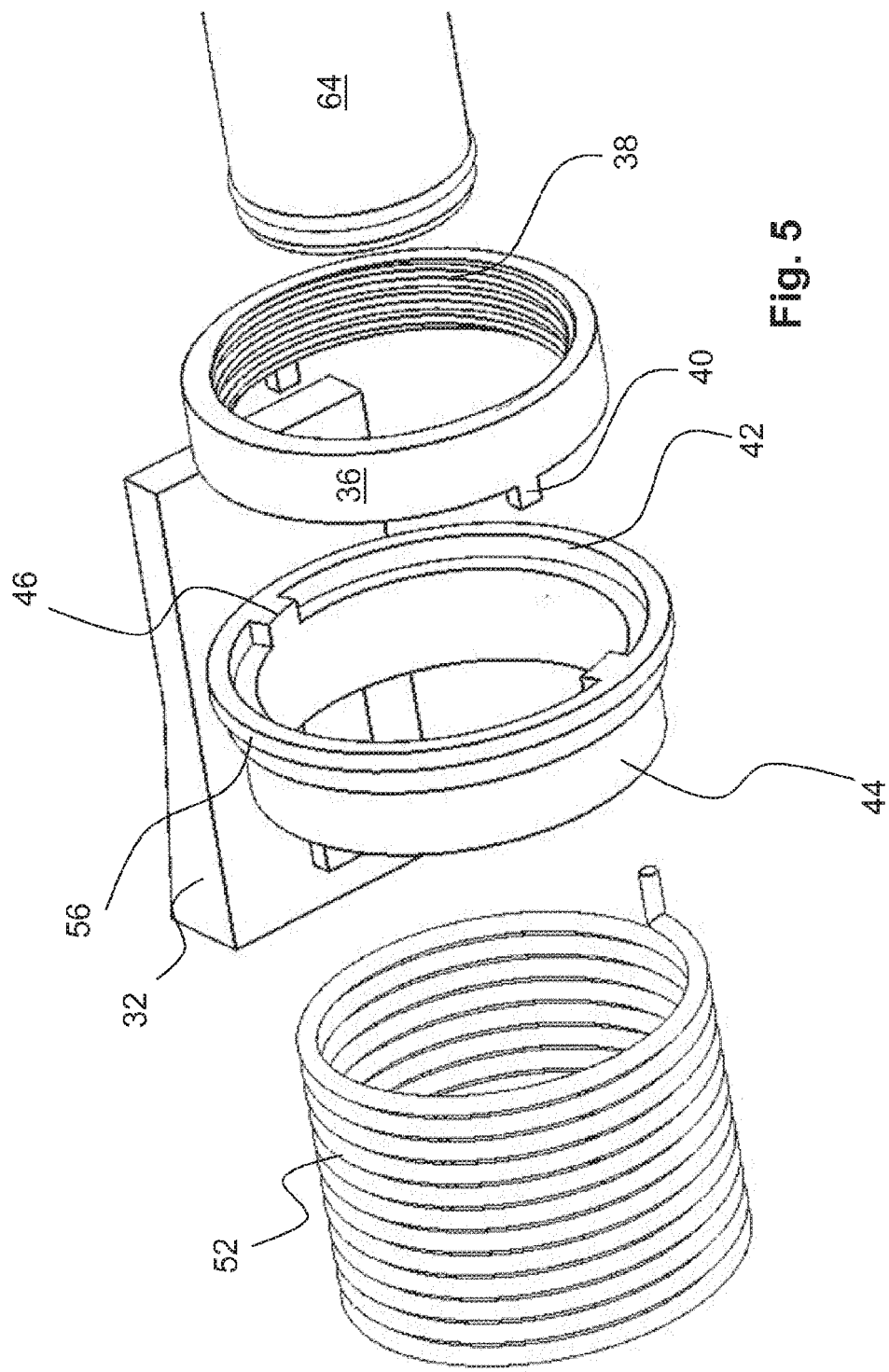

Further, the protective cap assembly comprises a nut 36, hereafter named drive nut, which is arranged with threads 38, FIG. 5, on its inner cylindrical surface, forming a first disconnecting means. The threads 38 are designed to cooperate with the threads 14 of the neck portion 12 of the front shell 10. A proximally directed end surface of the drive nut 36 is arranged with a number of proximally directed protrusions 40, FIG. 6. These protrusions 40 are arranged to fit into a circumferentially extending cut-out 42 on an inner surface of a ring-shaped drive member 44, FIG. 5, which drive member 44 is comprised in the first disconnecting means. The circumferential cut-out 42 is arranged with a number of distally directed ledges 46, FIG. 5, such that the protrusions 40 of the drive nut 36 engage the ledges 46, causing a rotational lock between the drive nut 36 and the drive member 44.

The outer surface of the drive member 44 is further arranged with a ledge 48, FIG. 6, which ledge 48 is designed to cooperate with the actuation member 34 such that a rotational lock is obtained of the drive member 44 when the actuation member 34 is in a position in engagement with the ledge 48 of the drive member 44. The drive member 44 is further arranged with an attachment point 50, FIG. 6, for a drive spring 52, also comprised in the first disconnecting means. In the embodiment shown the drive spring 52 is a torsion spring having a distal end 54, FIG. 5, which fits in a hole of the attachment point 50 of the drive member 44. The drive member 44 is arranged with a circumferential ledge 56 on its outer surface, which ledge is arranged to fit into seats 58, FIG. 4, on the inner surface of the protective cap 26, providing a relative locking in the longitudinal direction but allowing rotation of the drive member 44 in relation to the protective cap 26.

Figure 4:
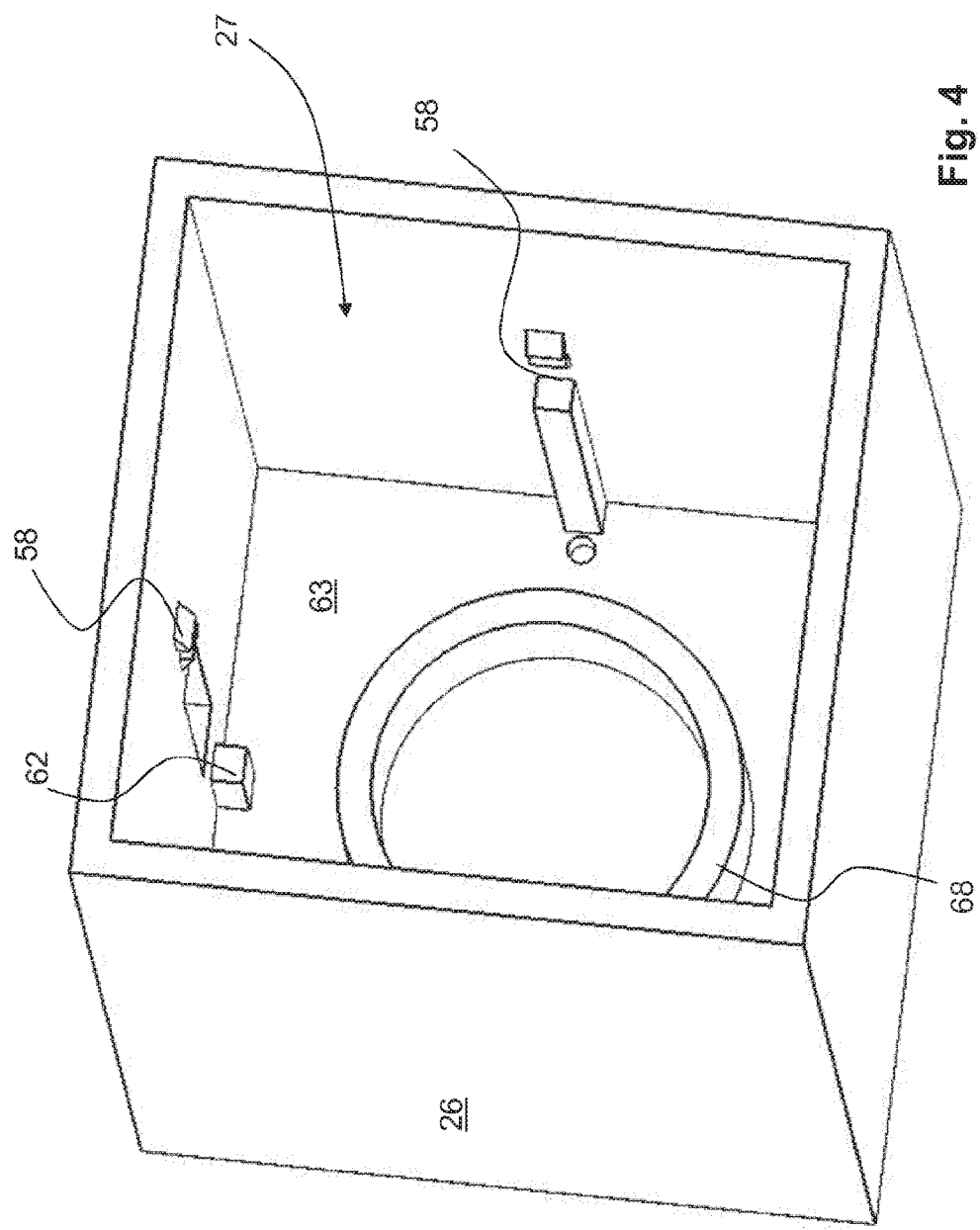

A proximal end 60 of the torsion drive spring is arranged to be engaging a ledge 62, FIG. 4, on a distally directed end surface 63, FIG. 4, in the interior of the protective cap 26, where the end surface 63 forms second disconnecting means of the protective cap 26. A shield remover 64 is further attached to the protective cap, forming a third connecting means. The shield remover 64 comprises a cylindrical member provided with a circumferential outwardly protruding ledge 66, FIG. 2, at its proximal end. The proximal end in turn fits into a cylindrical seat 68 on a distally directed end surface of the protective cap 26, where the cylindrical seat 68 is arranged with a circumferential groove, into which the circumferential ledge 66 of the shield remover 64 fits, such that the shield remover 64 is locked with the protective cap 26. The shield remover 64 is further arranged with tongues 68 at its distal end, which tongues 68 are directed in the proximal direction and inclined with respect to the longitudinal direction of the device.

The device according to the present invention is intended to be attached to the front shell 10 such that the drive nut 36 is threaded onto the neck portion 12 of the front shell 10. A medicament container 16 with an RNS 22 is fitted into the front shell 10.

The drive spring 52 is placed into the protective cap with its proximal end 60 in engagement with the ledge 62 and the drive member 44 is attached to the distal end 54 of the drive spring 52. Then the drive member 44 is pushed into the protective cap and locked into the seats 58 of the protective cap 26. The push button 32 is pushed in the proximal direction, which allows the drive member 44 to be rotated with a suitable tool (not shown) until the drive spring 52 has been tensioned a certain amount. Then the push button 32 is pushed back in the distal direction whereby the actuation member 34 is moved in engagement with the protrusion 48 of the drive member 44, thereby rotationally locking the drive member 44 with a tensioned drive spring 52.

The protective cap assembly 24 is then pushed onto the front shell 10, whereby the shield remover 64 encloses the rigid shell of the RNS 22. During the movement of the shield remover 64 in relation to the RNS 22, the inclined tongues 68 will come in contact with the rigid shell and flex radially outwards and slide along the outer surface of the rigid shell. When the protective cap 26 has been pushed in position on the front shell 10, and held there by frictional contact, the proximally directed protrusions 40 of the drive nut 36 fit into the groove 42 of the drive member 44. The device is now ready to be used. This initial position is shown in FIG. 1.

When a user now intends to administer a dose of medicament, first the protective cap assembly 24 has to be removed. The user then pushes the button 32 of the activation mechanism in the proximal direction. This causes the actuation member 34 to be moved out of contact with the ledge 48 of the drive member 44. The drive member 44 is now free to rotate and will do so due to the force of the torsion spring 52. Due to the rotational lock between the drive member 44 and the drive nut 36, the latter will also rotate along the threads 14 of the front shell 10, whereby the drive nut 36 is moved in the proximal direction. This movement in the proximal direction forces the whole protective cap assembly 24 in the proximal direction, including the shield remover 64. The inclined tongues 68 of the shield remover 64 will in turn grip into the rigid shell of the RNS 22, whereby also the RNS 22 will be moved in the proximal direction. The length of the threaded neck portion 12 and the strength of the drive spring 52 is designed such that the drive nut 36 is rotated until the protective cap 26 is removed from the front shell 10 as well as the RNS 22 is removed from the injection needle 20 of the medicament container 16, whereby the protective cap 26 falls off or is lifted off. The rotation of the drive nut 36 is thus stopped and it merely rests on the neck portion 12 of the front shell 10. The device is now ready for penetration and injection of medicament.

It is of course possible to remove the protective cap assembly 24 from the medicament delivery device purely manually without activating the automatic protective cap remover. The user may merely grip the protective cap and pull it in the proximal direction against the friction force between the protective cap and the front shell and the friction between the injection needle and the sheath.

FIGS. 7-12 show a second embodiment of the present invention. It comprises a front shell 110 of a medicament delivery device. The front shell 110 is arranged to accommodate a medicament container 112 having an injection needle 114 at its proximal end, which injection needle 114 is protected by a needle shield 116, in the embodiment shown a RNS. The RNS 116 is protruding through a proximally directed neck portion 118 of the front shell 110. A generally cylindrical actuator 120, forming first disconnecting means, is arranged on the neck portion 118 and having a distally directed end surface in contact with a shoulder portion 122 of the front shell 110 surrounding the neck portion 118, which shoulder portion 122 forms second disconnecting means of the housing. The actuator 120 is further arranged with a radially directed shoulder 124.

Figure 8:
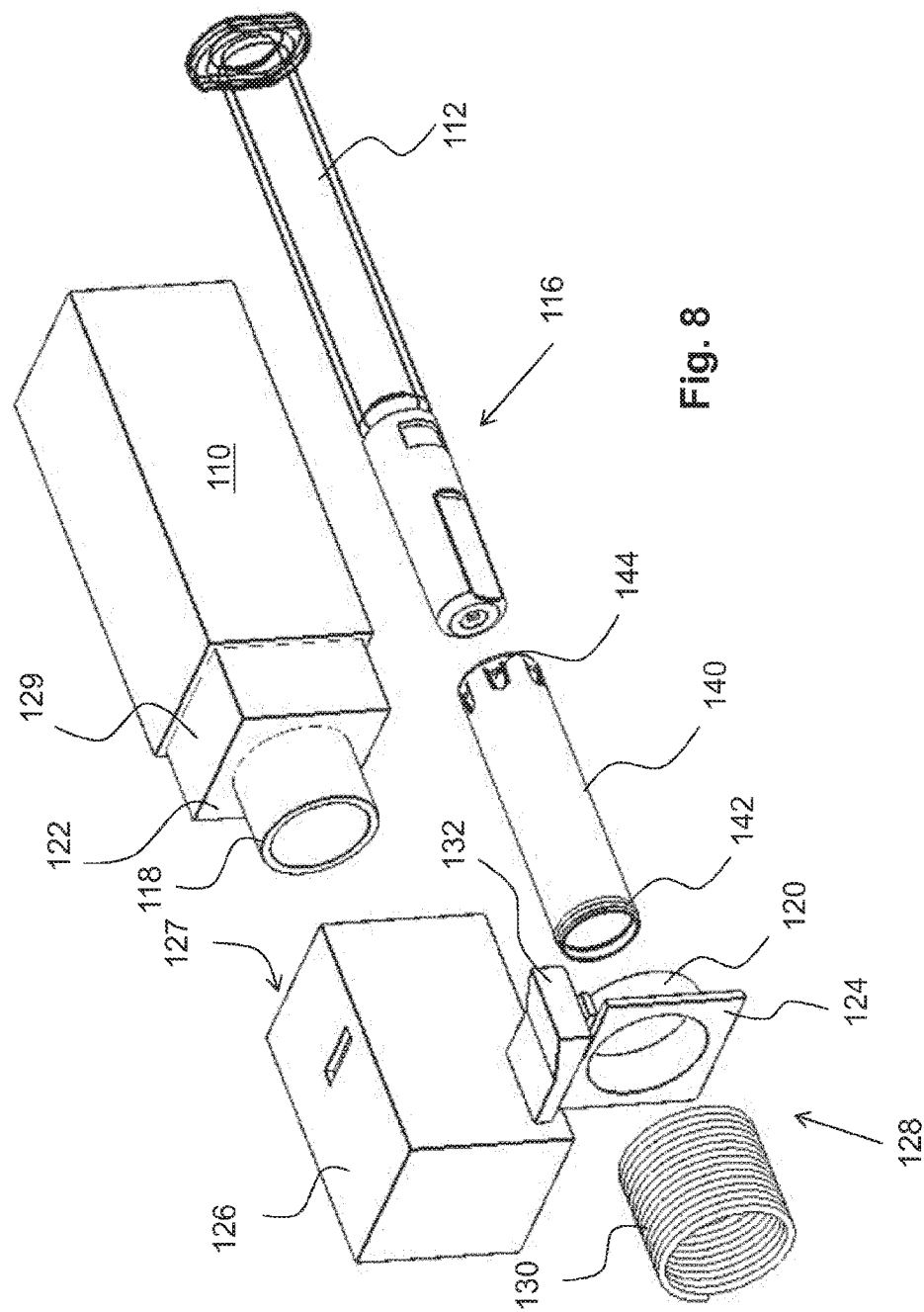
FIG. 8 is an exploded view of the embodiment of FIG. 7, FIGS. 9-11 are detailed views of components comprised in the embodiment of FIG. 7.

The actuator 120 is intended to fit into a protective cap 126 comprised in a protective cap assembly 128 of the invention, FIG. 8, where the shoulder portion 124 of the actuator 120 has a shape corresponding to the interior shape of the protective cap 126, thereby providing a rotational lock of the actuator 120 in relation to the protective cap 126. The protective cap 126 is arranged at the proximal end of the medicament delivery device having a distally directed opening 127 arranged to be pushed onto a recessed portion 129, forming a first connection means, of the front shell 110 and held there by friction, where the opening 127 forms second connecting means. Further a compression spring 130, comprised in the first disconnecting means, is arranged between a distally directed interior surface 131 of the protective cap 126 and a proximally directed end surface of the actuator 124, where the interior surface 131 second disconnecting means of the protective cap.

Figure 9:
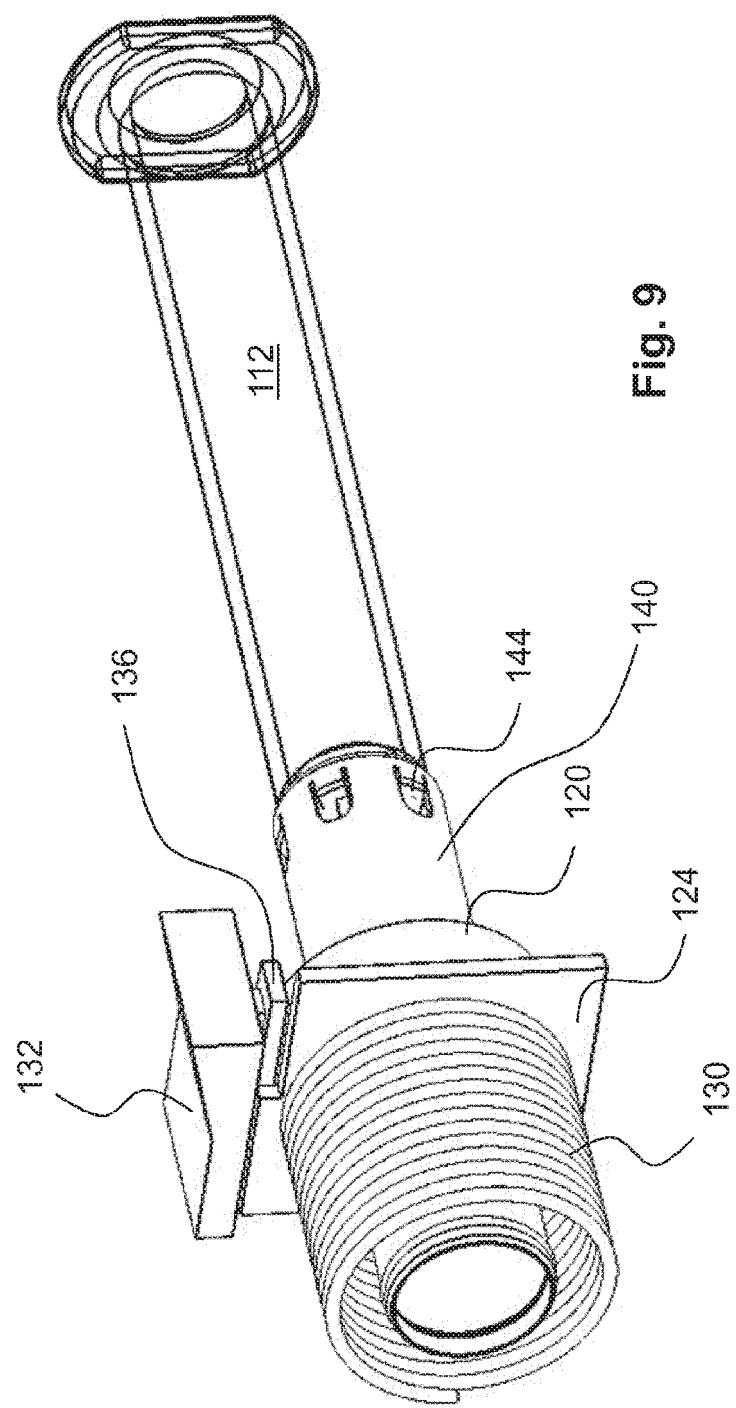
Figure 10:
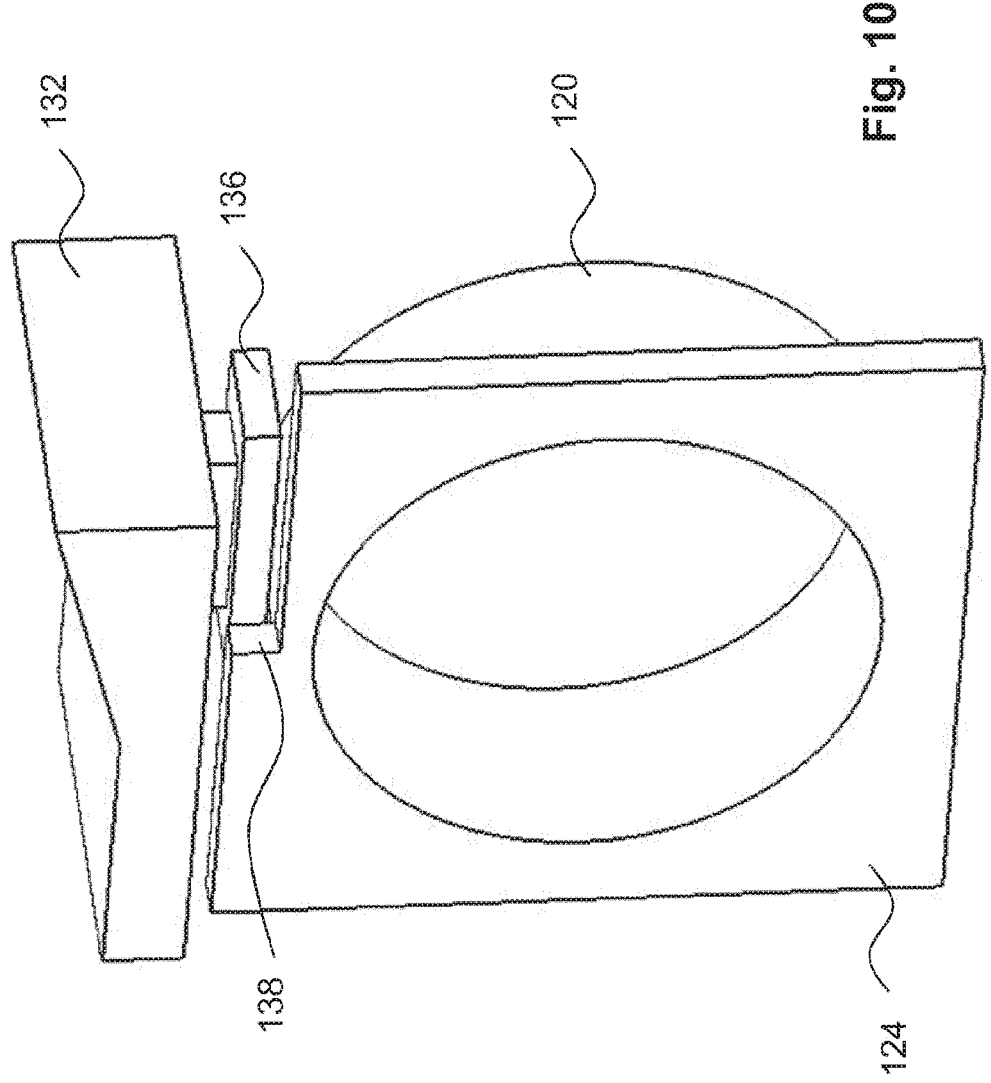
Figure 11:
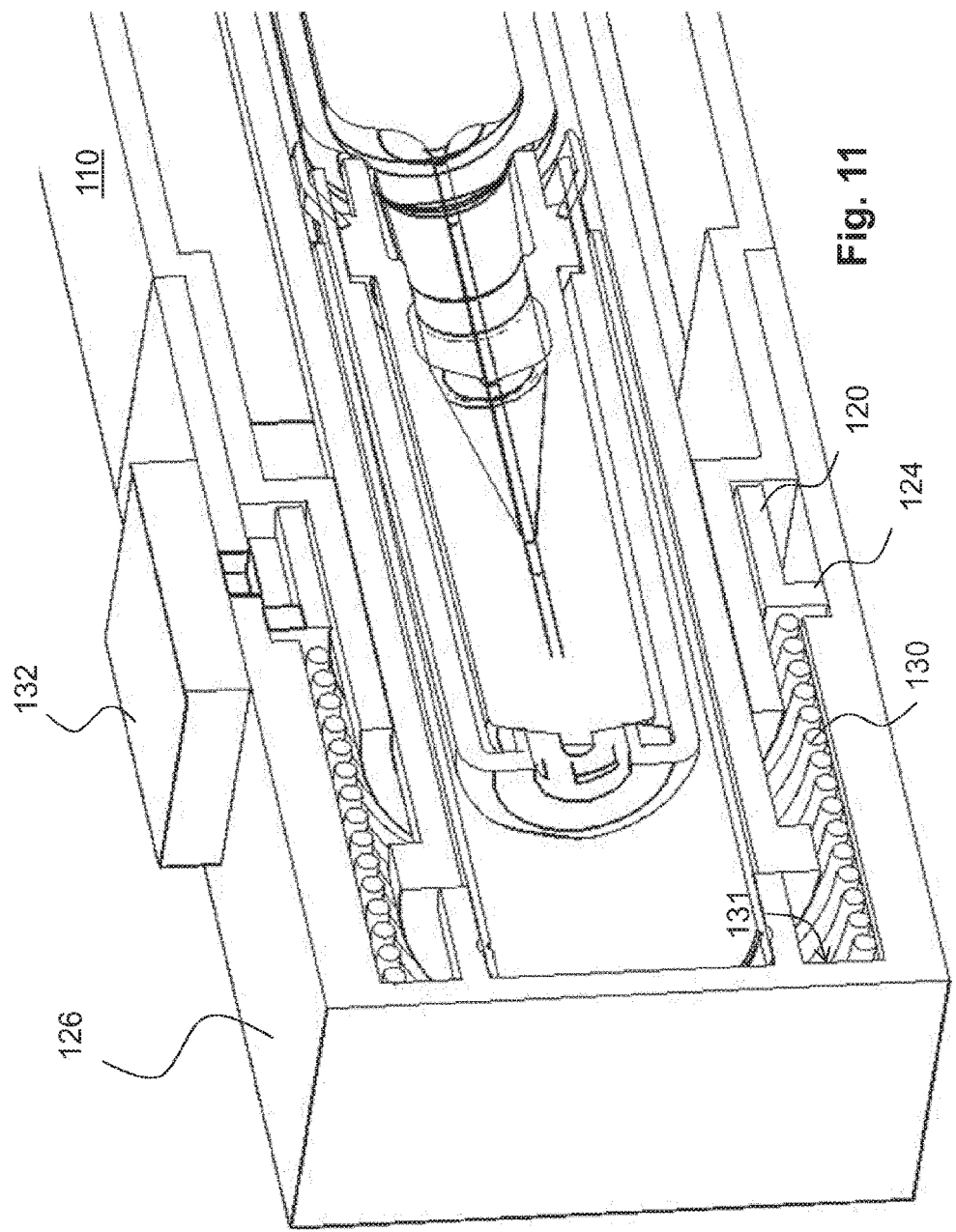

The protective cap assembly 128 further comprises an actuating mechanism including an activation member on an outer surface of the protective cap, in the embodiment shown a button 132, FIG. 9, slidable in a direction transversal to the longitudinal direction 134 of the device. The button 132 extends through an opening of the protective cap 126 and is attached to a plate-shaped actuation member 136, comprised in the actuating mechanism. The actuation member is in an initial position in contact with a distally directed surface of the shoulder of the actuator, FIG. 9. The shoulder portion is further arranged with a cut-out 138, FIG. 10, adjacent the actuation member 136.

A shield remover 140, FIG. 8, is further attached to the protective cap, which shield remover forms third connecting means. The shield remover 140 comprises a cylindrical member provided with a circumferential outwardly protruding ledge 142 at its proximal end. The proximal end in turn fits into a cylindrical seat 143, FIG. 7, on a distally directed end surface of the protective cap, where the cylindrical seat is arranged with a circumferential groove (not shown), into which the circumferential ledge 142 fits, such that the shield remover 140 is locked with the protective cap 126. The shield remover is further arranged with tongues 144 at its distal end, which 144 tongues are directed in the proximal direction and inclined with respect to the longitudinal direction 134 of the device.

Figure 7:
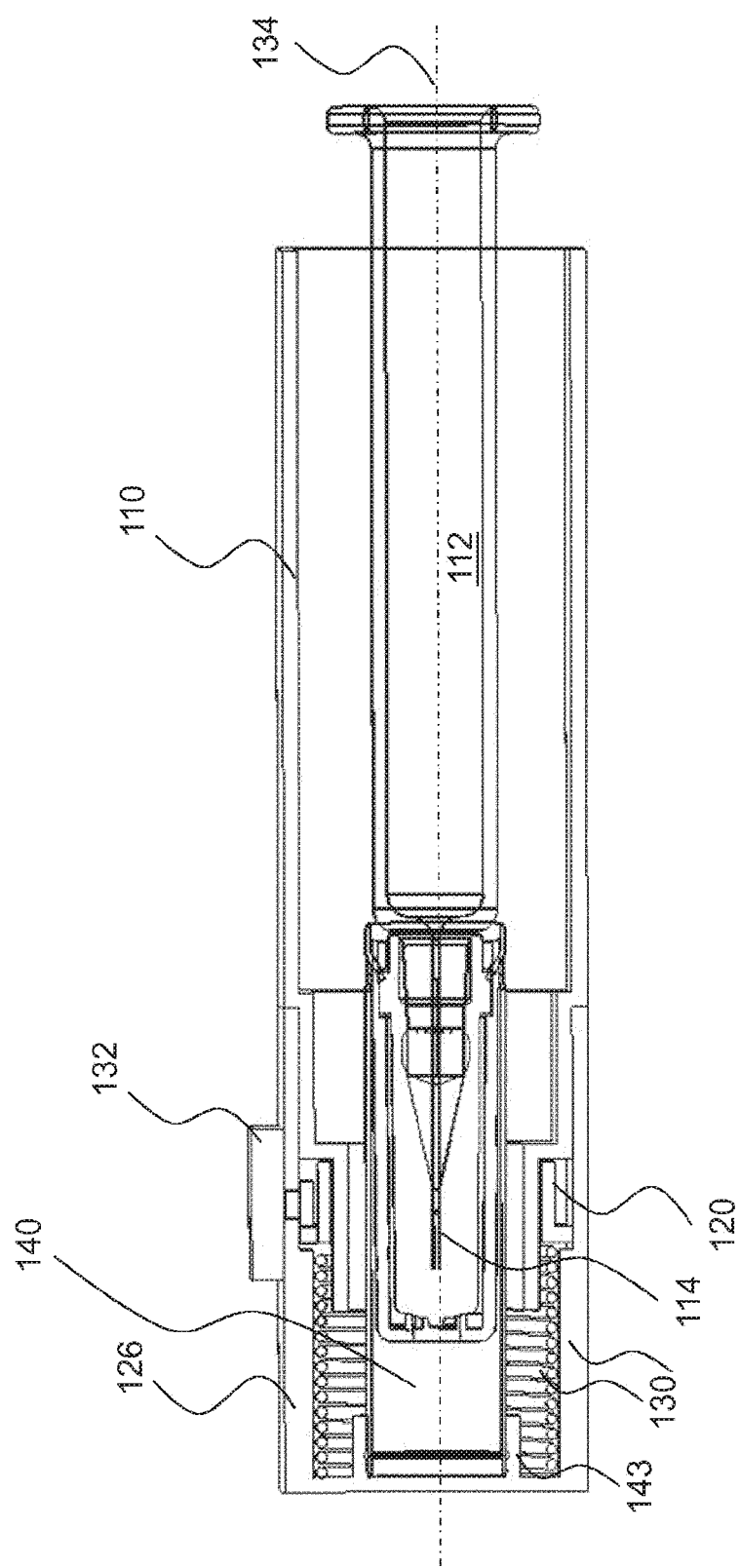
FIG. 7 is a cross-sectional view of a second embodiment of the present invention.

When the protective cap assembly 128 is to be arranged to the device, the compression spring 130 is placed inside the protective cap 126. The button 132 is then slid from the initial position after which the actuator 124 is pressed into the protective cap against the force of the spring 130, thereby compressing the latter. The button 132 is then returned to its initial position, whereby the spring 130 is held compressed inside the protective cap 126. The protective cap assembly 128 is then pushed onto the recessed portion 129 of the front shell 110, whereby the remover 140 encloses the rigid shell of the RNS 116. During the movement of the remover in relation to the RNS, the inclined tongues 144 will come in contact with the rigid shell and flex radially outwards and slide along the outer surface of the rigid shell. When the protective cap 126 has been pushed in position on the front shell, and held there by frictional contact, a distally directed surface of the actuator 120 is in contact with the shoulder portion 122 of the front shell, as shown in FIG. 7. The device is now ready to be used.

When a user now intends to administer a dose of medicament, first the protective cap assembly 128 has to be removed. The user then pushes the button 132 of the actuating mechanism in the transversal direction. This causes the actuation member 136 to be moved to the recess 138 of the shoulder 124 of the actuator, and thereby out of contact with the actuator 124, whereby the force of the compression spring 130 is released such that it presses the actuator 120 in the distal direction against the shoulder 122 of the front shell 110. The force of the spring 130 causes the protective cap 126 to be moved in the proximal direction against the friction forces between the protective cap 126 and the front shell 110 and the RNS and the injection needle respectively such that the protective cap assembly 128 with the needle shield 116 is removed, thereby exposing the injection needle 114. The device is now ready for penetration and injection of medicament.

It is of course possible to remove the protective cap assembly from the medicament delivery device purely manually without activating the automatic protective cap remover. The user may merely grip the protective cap and pull it in the proximal direction against the friction force between the protective cap and the front shell and the friction between the injection needle and the sheath.

FIGS. 12 to 17 show a third embodiment of the present invention. In this embodiment the medicament container with its needle shield as well as with its shield remover have been omitted, but it may readily be understood by the person skilled in the art that the same components and features described above may be applied to the third embodiment without departing from the inventive idea.

Figure 12:
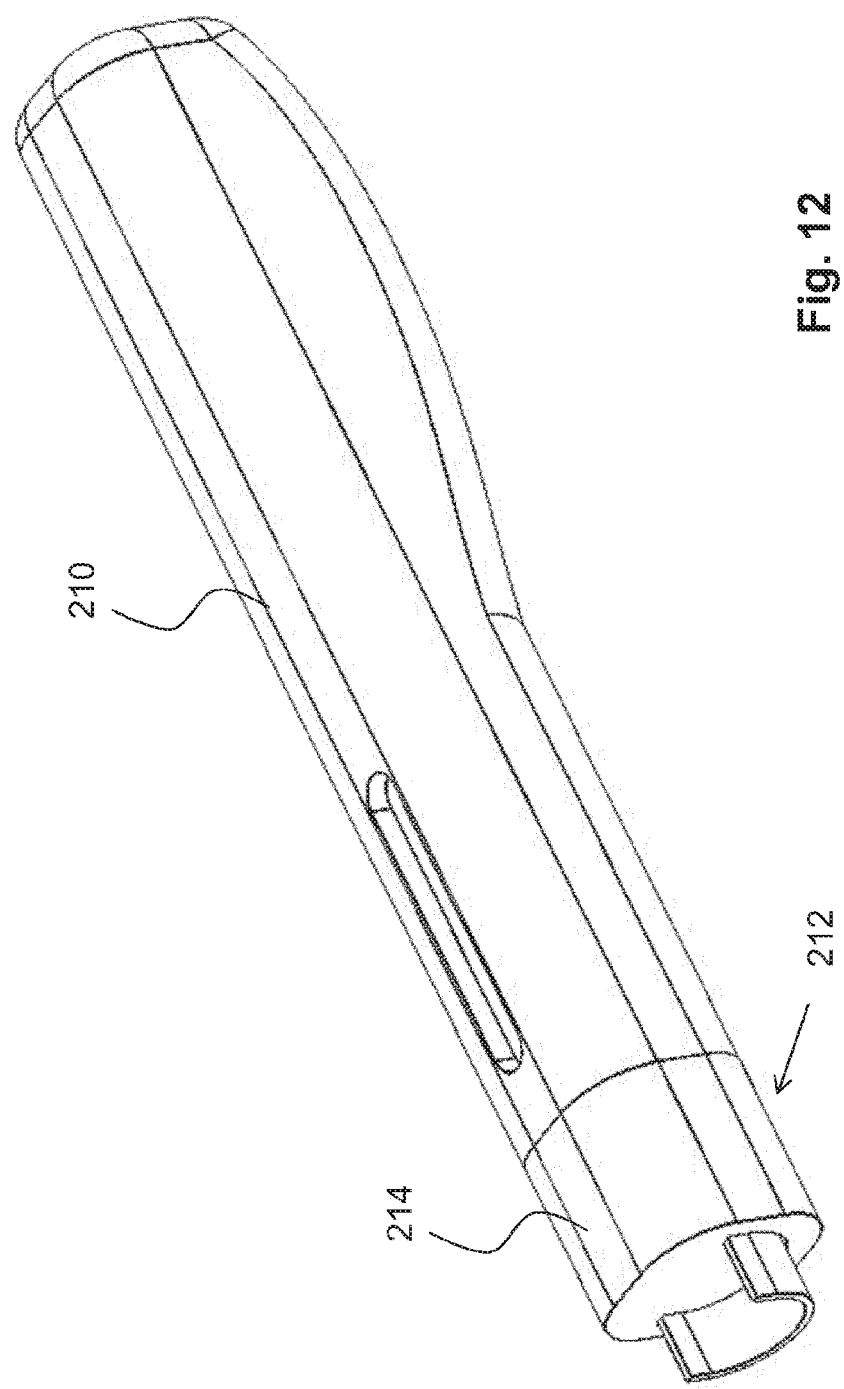
FIG. 12 is a perspective view of a third embodiment of the present invention.

A proximal end of a housing 210 of a medicament delivery device is arranged with a protective cap assembly 212, FIG. 12. The protective cap assembly 212 comprises a protective cap 214, FIG. 13, having a distally directed opening 215, forming second connecting means, and is designed to fit onto a recessed part 216, forming a first connecting means, at a proximal end of the housing and held there by certain friction between the protective cap 214 and the housing 210. The design of the protective cap 214 and the housing part 216 is such that the protective cap 214 is rotationally locked to the housing 210.

Figure 13:
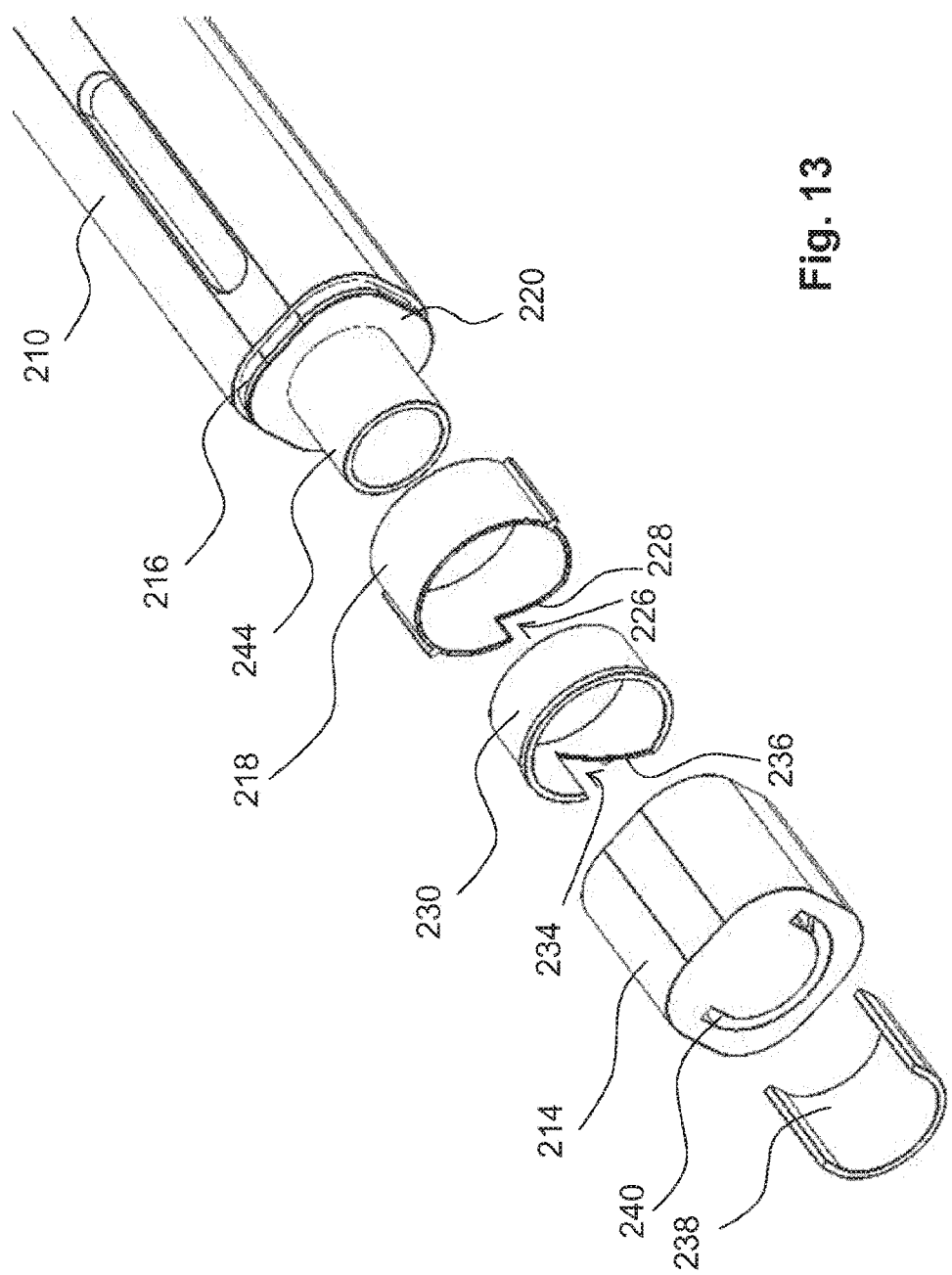
FIG. 13 is an exploded view of the embodiment of FIG. 12, FIGS. 14-15 are detailed views of components comprised in the embodiment of FIG. 12, FIGS. 16-17 are detailed views of the function of the embodiment of FIG. 12.

The protective cap assembly 212 further comprises a guide member 218, FIG. 13, of a generally tubular shape, forming a first disconnecting means. The guide member 218 is arranged to contact a proximal end surface 220 of the housing with a distal end surface, which proximal end surface 220 forms second disconnecting means. The guide member 218 is arranged with longitudinally extending guides 222, FIG. 14, which are arranged to fit in corresponding grooves 224 on inner surfaces of the protective cap 214. With this arrangement, the guide member 218 is rotationally locked to the protective cap 214 and thereby to the housing 210. A proximally directed end surface of the guide member 218 is arranged with a cut-out 226 having an inclined first surface 228, FIG. 13.

The protective cap assembly 212 further comprises a rotator 230 having a generally tubular shape, which rotator 230 is comprised in the first disconnecting means. The rotator 230 has a diameter somewhat smaller than the guide member 218 and arranged extending into the guide member. The rotator 230 is arranged with a radially outwardly extending protrusion 232, FIGS. 14 and 15, which protrusion 232 is designed to be in contact with the first inclined surface 228, as will be explained. The rotator 230 is further arranged with a cut-out 234 having an inclined second surface 236, FIG. 13.

Figure 14:
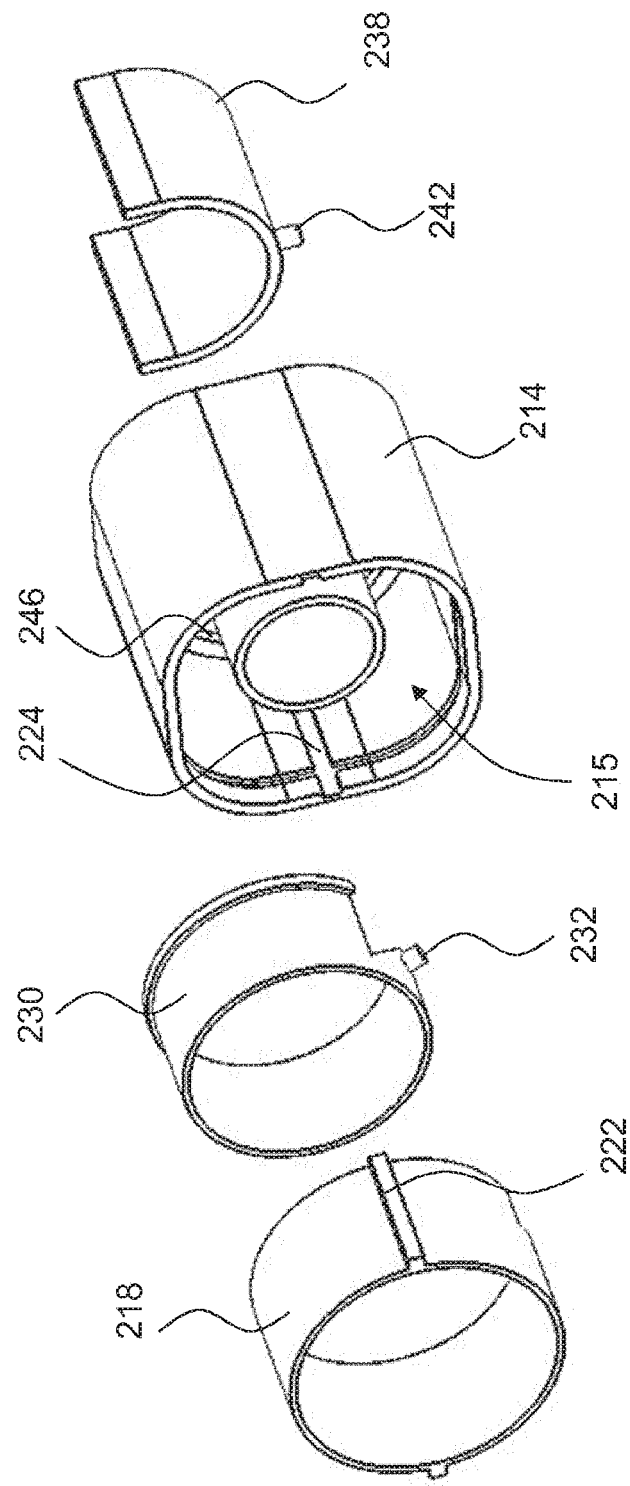
Figure 15:
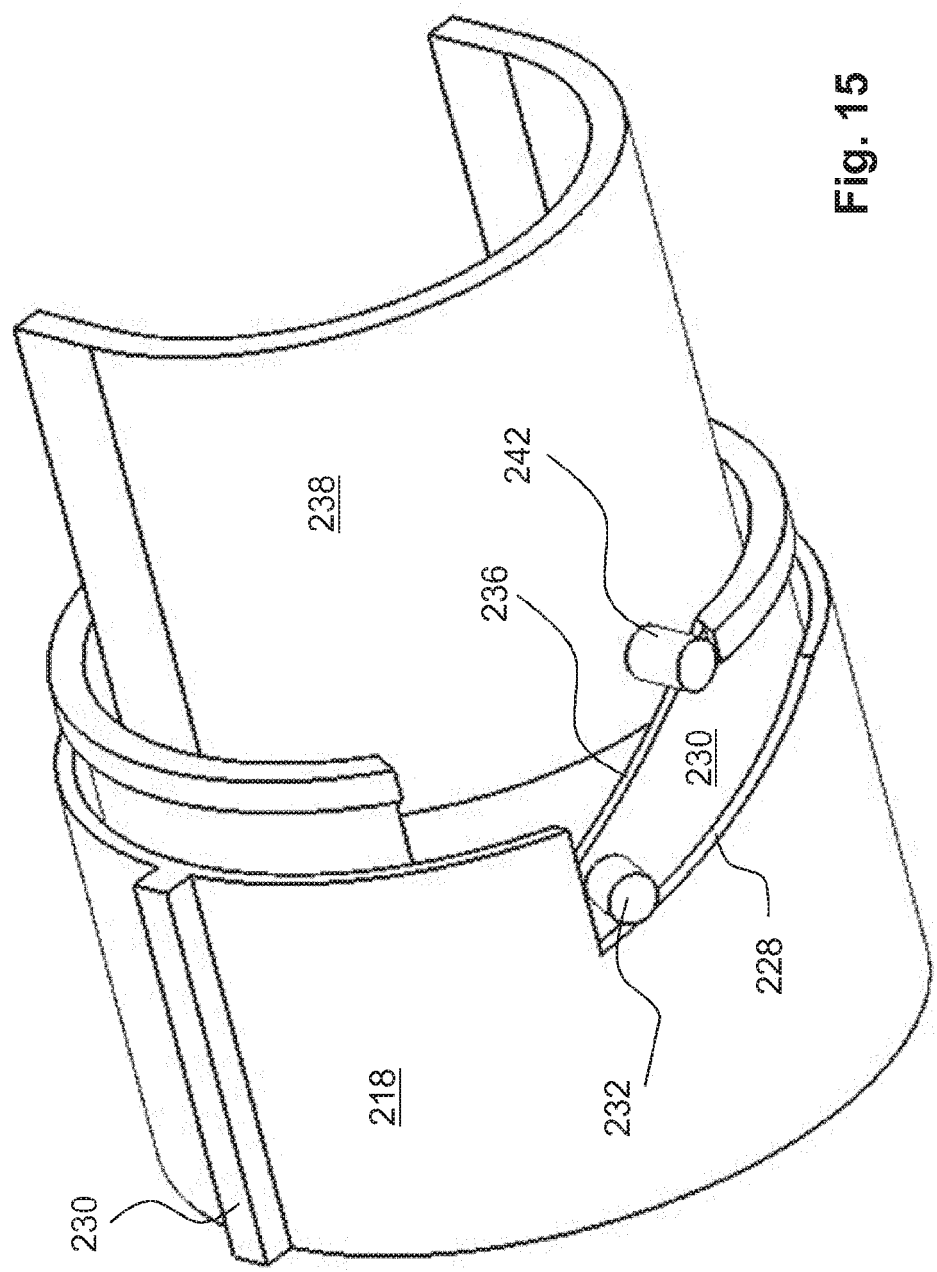
Figure 16:
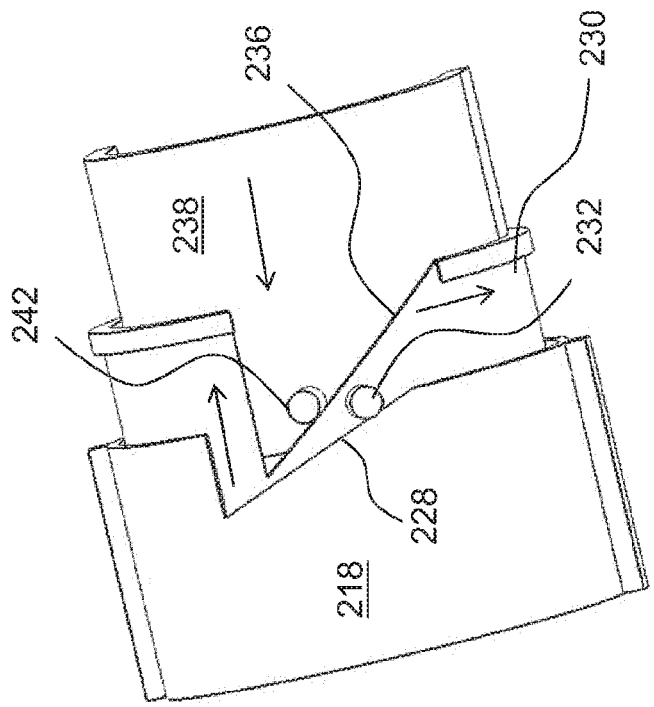
Figure 17:
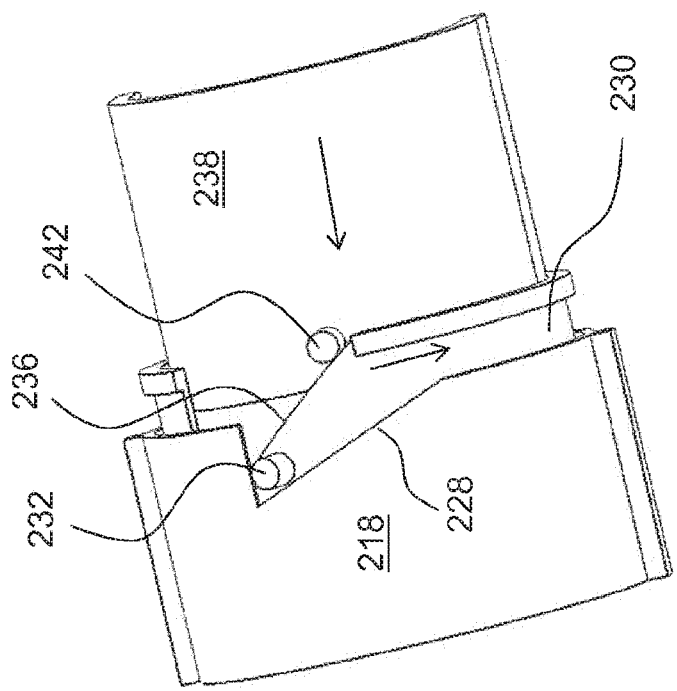
Figure 18:
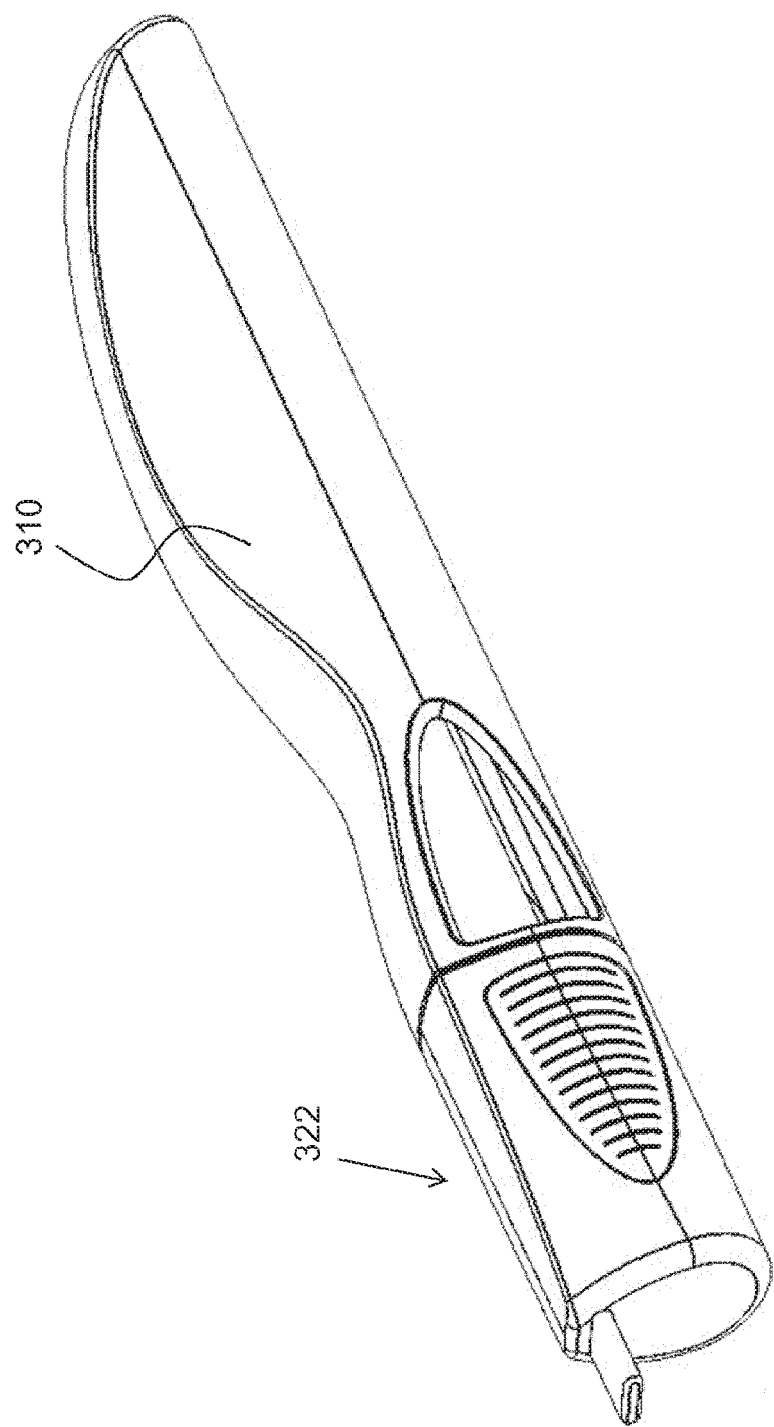
FIG. 18 is a perspective view of a fourth embodiment of the present invention.

The protective cap assembly 212 further comprises an actuator 238, FIGS. 13 and 14, having a general U-shape and arranged extending through an opening 240 in a proximal end surface of the protective cap 214, where the opening 240 has a shape corresponding to the shape of the actuator 238. The actuator 238 is further arranged with a radially extending protrusion 242, FIGS. 14 and 15, on a side surface, which protrusion 242 is designed to be in contact with the second inclined surface 236, as will be explained. The protective cap 214 is further arranged with a distally directed end surface 246, FIG. 14, forming second disconnecting means of the protective cap.

The third embodiment is intended to function as follows. When the protective cap assembly 212 is pushed onto the proximal end of the housing, it is held in place by friction between the protective cap 214 and the housing 210. Further a needle shield, such as an RNS, is extending through a neck portion 244, FIG. 13 of the housing. The needle shield is surrounded by a remover (not shown), forming a third connection means, which in turn is attached to the interior of the protective cap 214.

When a user is to remove the protective cap assembly for administering a dose of medicament, the medicament delivery device is gripped such that the proximal part of the device, including the protective cap assembly 212, may be pressed against a rigid surface. Thus, when the protective cap assembly 212 is pressed, the actuator 238 is forced in the distal direction into the protective cap 214. This linear movement causes the protrusion 242 of the actuator 238 to act on the second inclined surface 236 of the rotator 230, FIG. 16. Due to the inclination of the second surface 242 and the rotational lock of the actuator 238, the rotator 230 is forced to rotate.

The rotation of the rotator 230 causes its protrusion 232 to act on the first inclined surface 228 of the guide member 218. Due to the inclination of the first inclined surface 228 and the rotational lock of the guide member 218, the rotator 230 is moved in the proximal direction during rotation, FIG. 17. The rotator 230 is designed such that a proximal end surface thereof is in contact with the distally directed surface 246 of the protective cap 214 whereby a movement of the rotator 230 in the proximal direction causes also the protective cap 214 to be moved in the proximal direction against the friction force between the protective cap and the housing and the friction force between the needle shield and the injection needle.

When the actuator 238 has been pressed fully into the protective cap 214, the protective cap 214 has moved such in the proximal direction that it is out of contact with the housing 210 and may be completely removed. In this respect it is to be understood that the protrusions 232, 242 on the rotator 230 and the actuator 238 as well as the inclined surfaces 228, 236 of the guide member 218 and the rotator 230 are chosen such that the force requirements are kept moderate and that the stroke of the rotator 230 enables loosening of the protective cap assembly 212.

The third embodiment may also be completely manually removed in that a user may grip the protective cap and pull it in the proximal direction against the forces holding it in place, thereby pulling of the protective cap assembly from the medicament delivery device. An advantage with this solution is that the initial grip of the device for removing the protective cap assembly may be continued during the subsequent penetration and injection. Thus, a user does not need to change grips during administration.

FIGS. 18 to 24 disclose a fourth embodiment of the present invention. It comprises a housing part 310 provided with a proximal area 312 having a reduced size in the general radial direction, providing a proximally directed ledge 314. Inside the housing part and protruding through the proximal area, a medicament container 316 is arranged to be positioned. A proximal end of the medicament container 316 is arranged with a medicament delivery member 318, FIG. 20, either attached to or made integral with the medicament container 316. The medicament delivery member is covered by a protective needle shield 320, such as e.g. an RNS or an FNS. In the embodiment shown, the shield is a FNS.

A protective cap assembly 322 is further provided to the device. It comprises a protective cap 324 having a generally tubular shape with a distally directed opening 326, FIG. 21. The shape and the dimensions of the opening 326 is such that it fits onto the proximal area 312 of the housing with a certain friction, with a distally directed end surface 327 in contact with the ledge 314 of the housing 310. An inner, distally directed, surface 328 of an end wall 330 of the protective cap is arranged with a generally tubular member 332, extending in the distal direction. On the inner surface of the tubular member 332, a number of grip members 334 are arranged, FIG. 21, designed as wedge-shaped protrusions, the function of which will be explained below.

Figure 19:
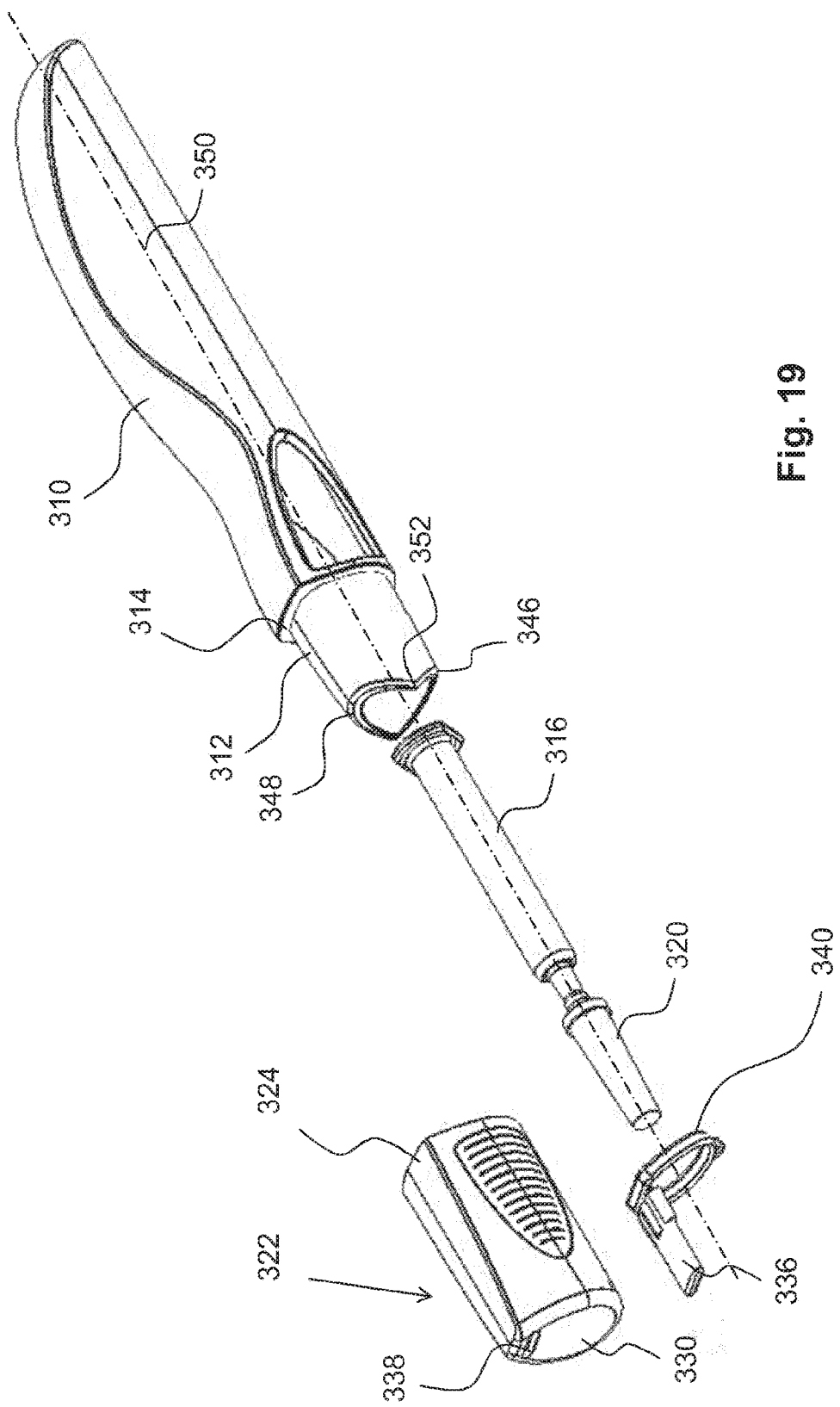
FIG. 19 is an exploded view of the embodiment of FIG. 18.
Figure 20:
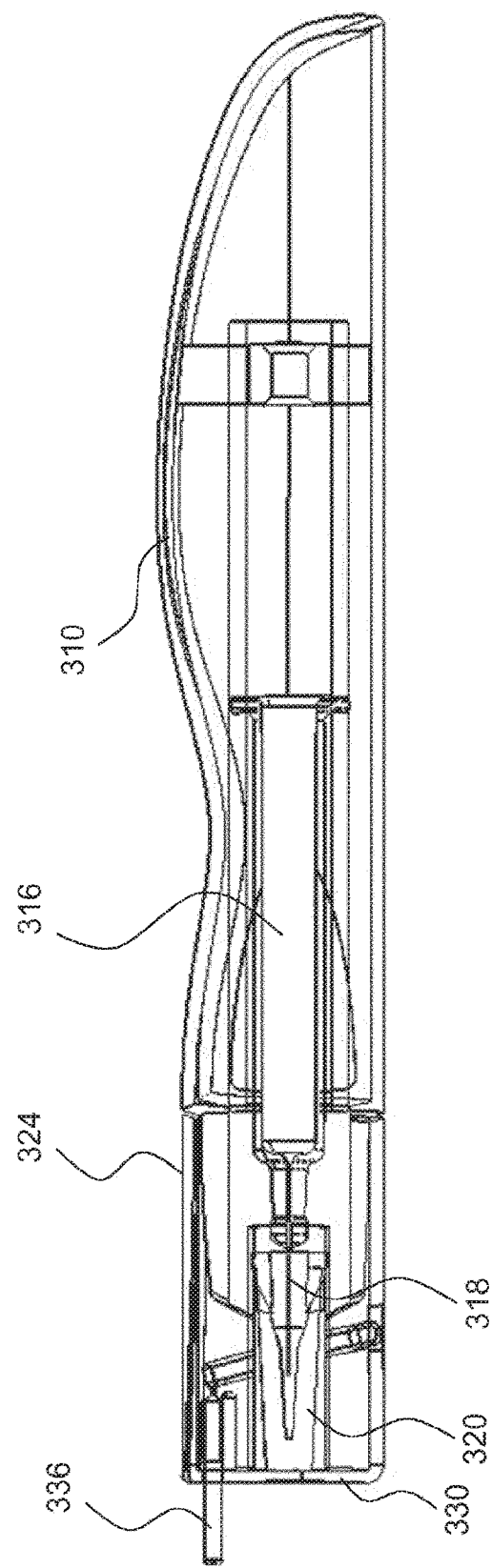
FIG. 20 is a perspective view of the embodiment of FIG. 18 with a protective cap removed.
Figure 21:
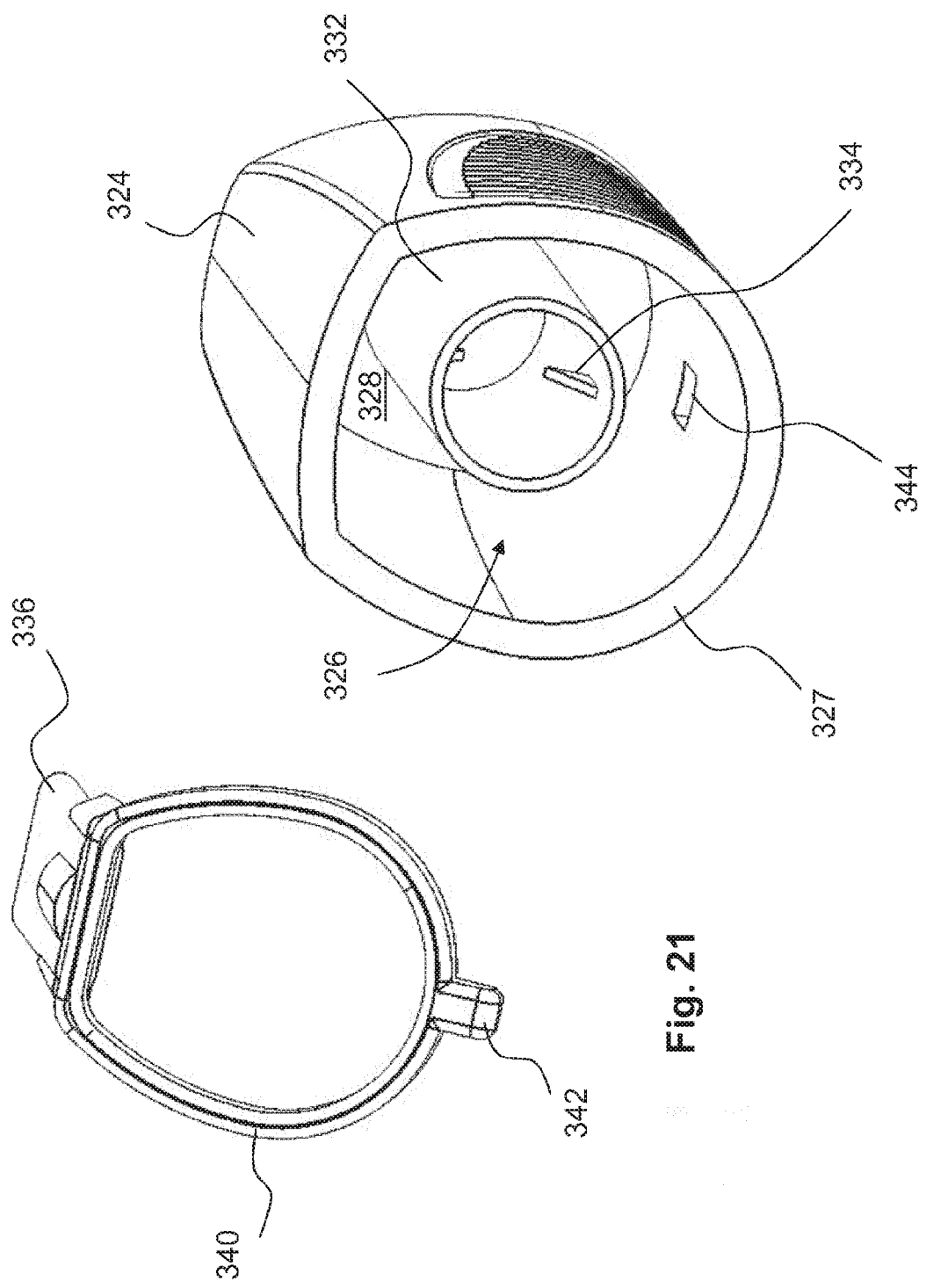
FIG. 21 is a detailed exploded view of a cap assembly of the embodiment of FIG. 18, FIGS. 22-23 are cross-sectional views of the function of the embodiment of FIG. 18.
Figure 22:
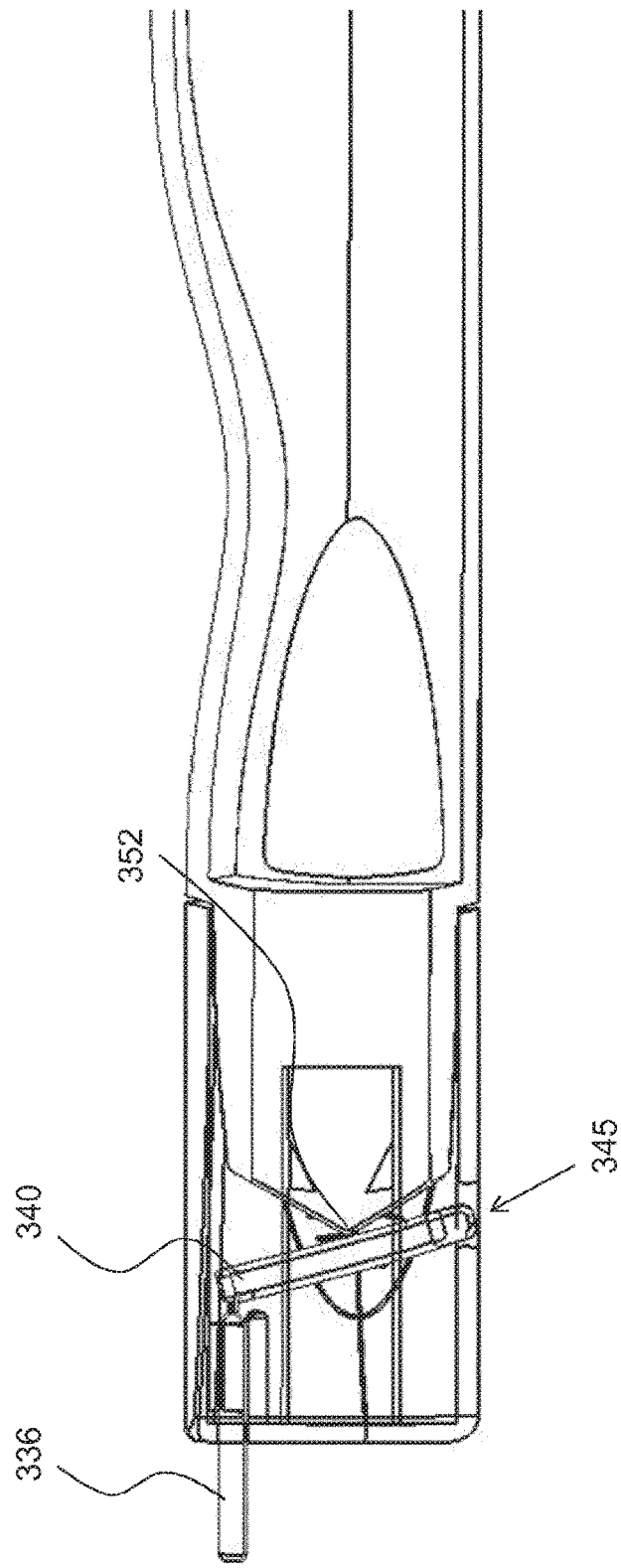
Figure 23:
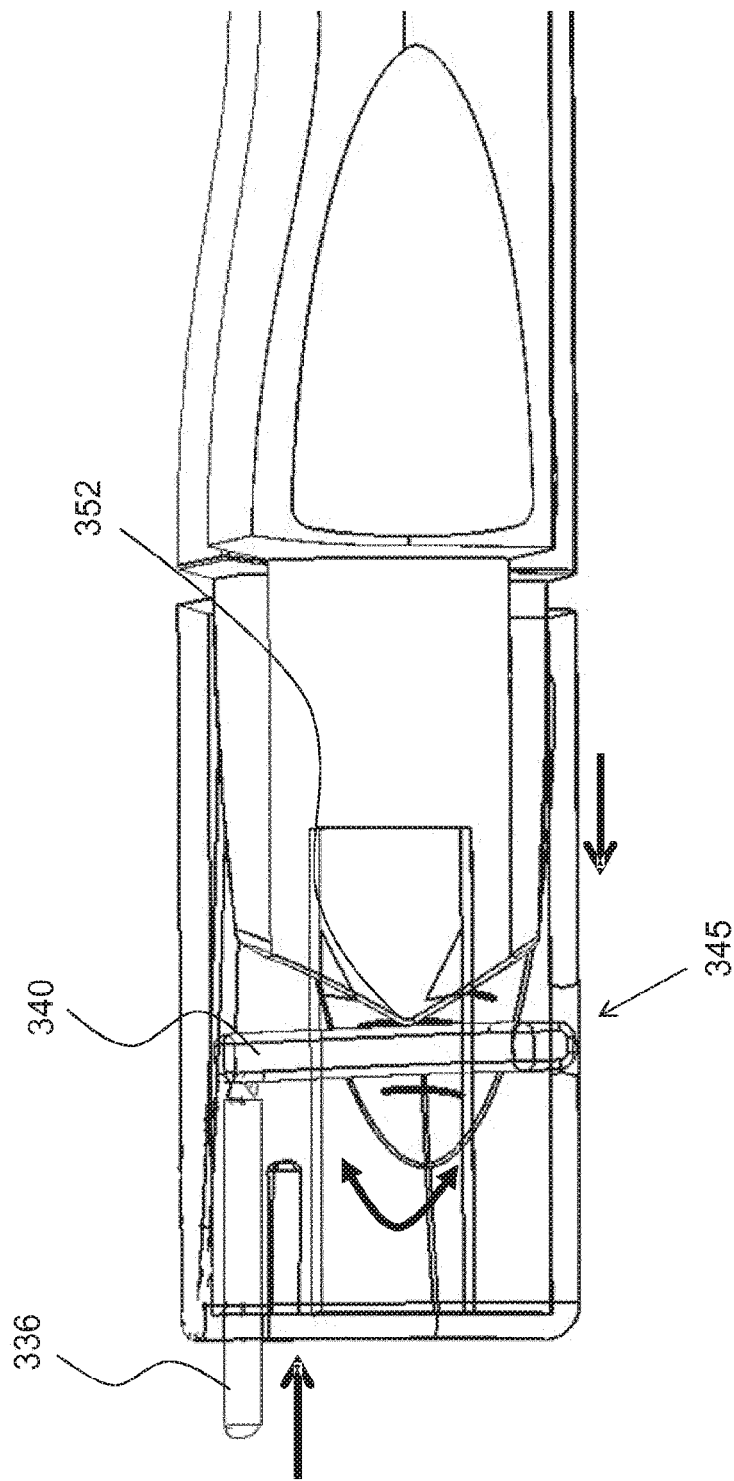
Figure 24:
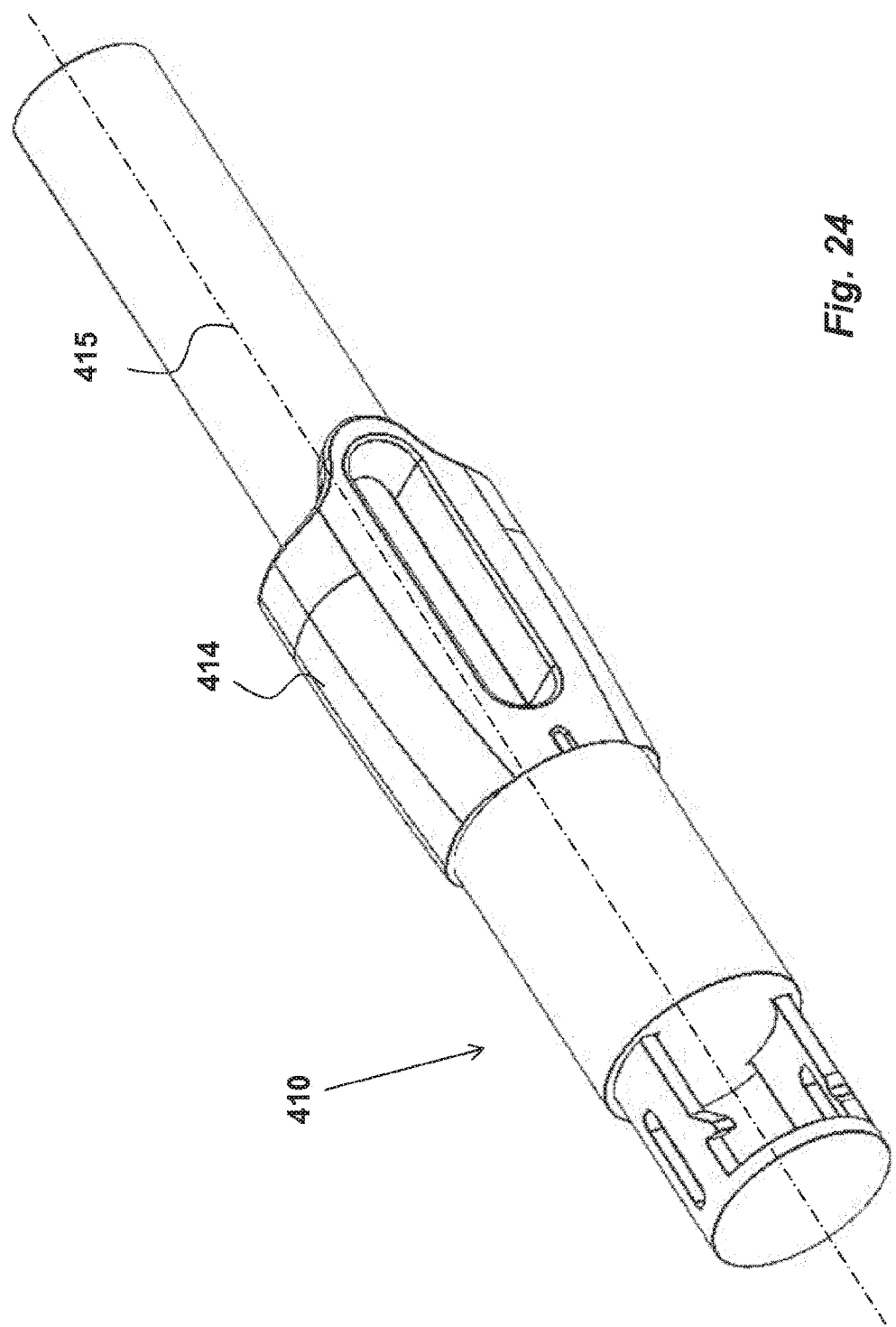
FIG. 24 is a perspective view of a fifth embodiment of the present invention.

An actuator member 336, FIG. 21, is arranged to the protective cap 324, in the form of an elongated member arranged slidable and protruding through a passage 338, FIG. 19, in the end wall 330 of the protective cap. A distal end of the actuator member 336 is attached to, or made integral with, a ring-shaped activation member 340, FIG. 21, such that the connection between the actuator member 336 and the activation member 340 provides some hinge action. On an opposite end of the ring-shaped activation member 340 in relation to the hinge connection, a generally radially outwardly directed protrusion 342 is arranged. The protrusion is intended to fit into a recess 344 on an inner side surface of the protective cap 324, providing a hinge 345, FIG. 22, 23. Further, the proximally directed end surface of the housing is arranged in two sections 346, 348, FIG. 19, inclined with respect to a longitudinal direction 350 of the device, whereby two pointed projections 352 are obtained.

The device is intended to function as follows. The safety cap assembly 322 is arranged such that the ring-shaped activation member 340 is placed inside the protective cap 324 with its protrusion 342 in the recess 344 and the actuation member 336 extending through the opening of the protective cap 324. The protective cap assembly 322 is pushed onto the proximal, recessed, end 312 of the housing 310, which housing 310 contains a medicament container 316 with its medicament delivery member 318 covered by a shield 320. When the protective cap 324 is pushed onto the housing, the tubular member 332 of the protective cap surrounds the shield 320, FIG. 20. The wedge-shaped grip members 334 slide along the surface of the shield 320 until the distal end surface comes in contact with the ledge 314, FIG. 22.

When the protective cap 324 is to be removed, the proximal end of the device, and thus the protective cap assembly 322, is pressed against a firm surface. This causes the actuation member 336 to be pushed in the distal direction, FIG. 22, in relation to the protective cap 324. The movement in the distal direction of the actuation member 336 causes the ring-shaped activation member 340 to be also moved in the distal direction due to the inter-connection between the two. However, due to that the opposite side of the ring-shaped activation member 340 is attached to the protective cap via the hinge 345 and due to the pointed projections 350, which are placed generally between the hinge 345 and the connection of the actuation member 336, the ring-shaped activation member 340 will pivot around the pointed projections 350, FIG. 23. In turn, this pivot action causes the hinge 345 to move in the proximal direction, and thus the protective cap 324 to move in the proximal direction, whereby the protective cap 324 is pushed off the housing part against the friction force between the protective cap and the housing part 312. Because of the grip members 334 gripping into the shield 320, the shield 320 will also be pushed off the medicament delivery member 318. When the protective cap assembly is removed, the device is ready for medicament delivery.

It is to be understood that the fourth embodiment may also be completely manually removed in that a user may grip the protective cap and pull it in the proximal direction against the forces holding it in place, thereby pulling of the protective cap assembly from the medicament delivery device. An advantage with this solution is also that the initial grip of the device for removing the protective cap assembly may be continued during the subsequent penetration and injection. Thus, a user does not need to change grips during administration.

A fifth embodiment of a medicament delivery device comprising a protective cap assembly 410 according to the present invention is shown in the drawings 24 to 35. It comprises a generally tubular sleeve, hereafter named ejector sleeve 412, FIG. 25. The inner diameter of the ejector sleeve 412 is chosen somewhat larger than a proximal end part of a housing 414 of the medicament delivery device, e.g. a front shell, which proximal end may for example comprise an activation member 416 slidable along a longitudinal axis 415 of the device for activating e.g. penetration and injection of the device. The ejector sleeve 412 is arranged with a circumferential outwardly directed ledge 418 at its distal end, FIGS. 26 and 27. A distal surface of the ledge 418 is intended to be in contact with a proximally directed circumferential surface area 420, FIG. 25 of the medicament delivery device, comprised in second disconnecting means of the housing. The ejector sleeve 412 is further arranged with circumferential inwardly directed ledge 422 at its proximal end, FIG. 27, forming a circularly shaped passage 424. The ledge 422 is arranged with a number of slits 426, the function of which will be described below.

Figure 25:
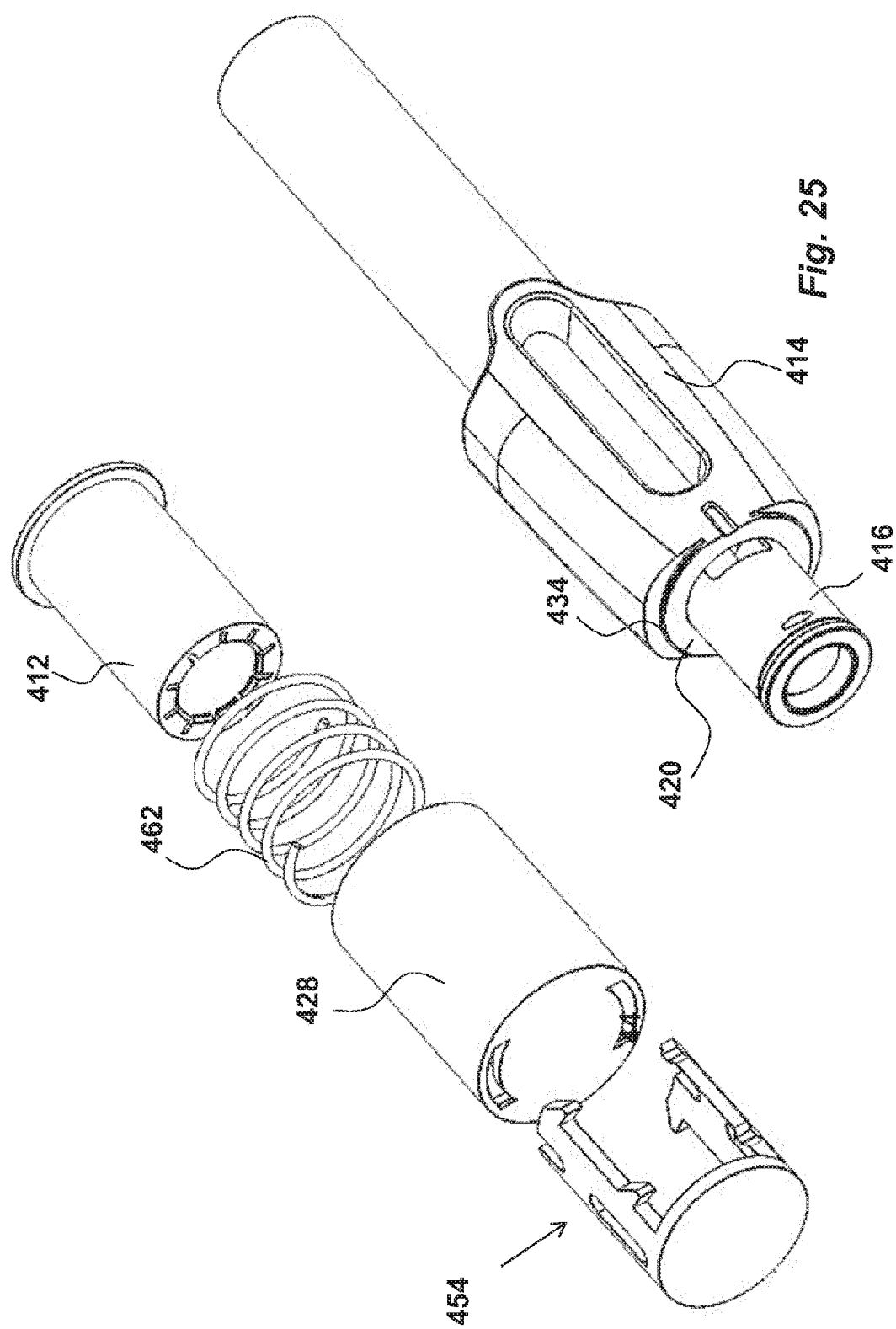
FIG. 25 is an exploded view of the embodiment of FIG. 24, FIGS. 26-27 are detailed views of components comprised in the embodiment of FIG. 24.
Figure 26:
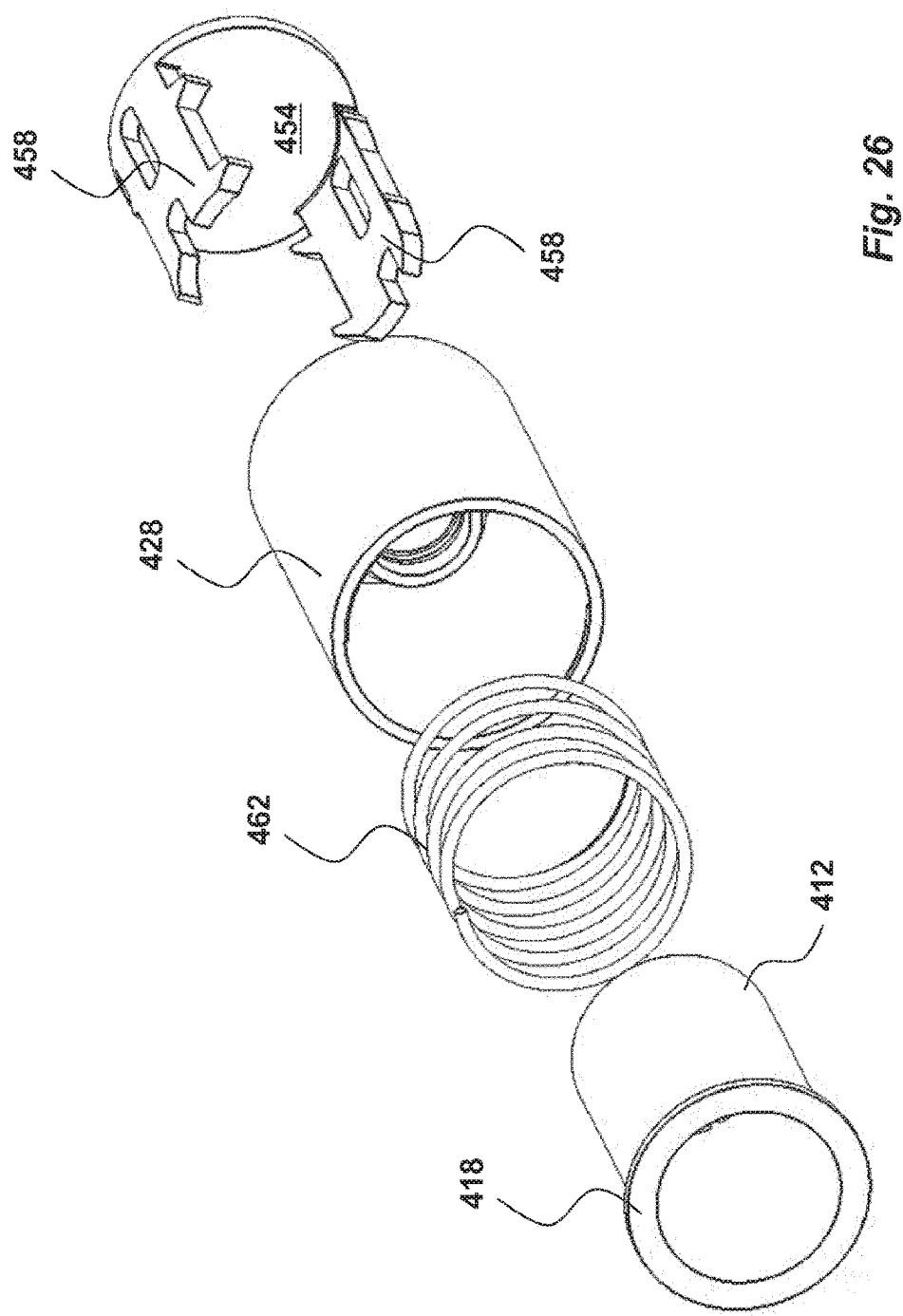
Figure 27:
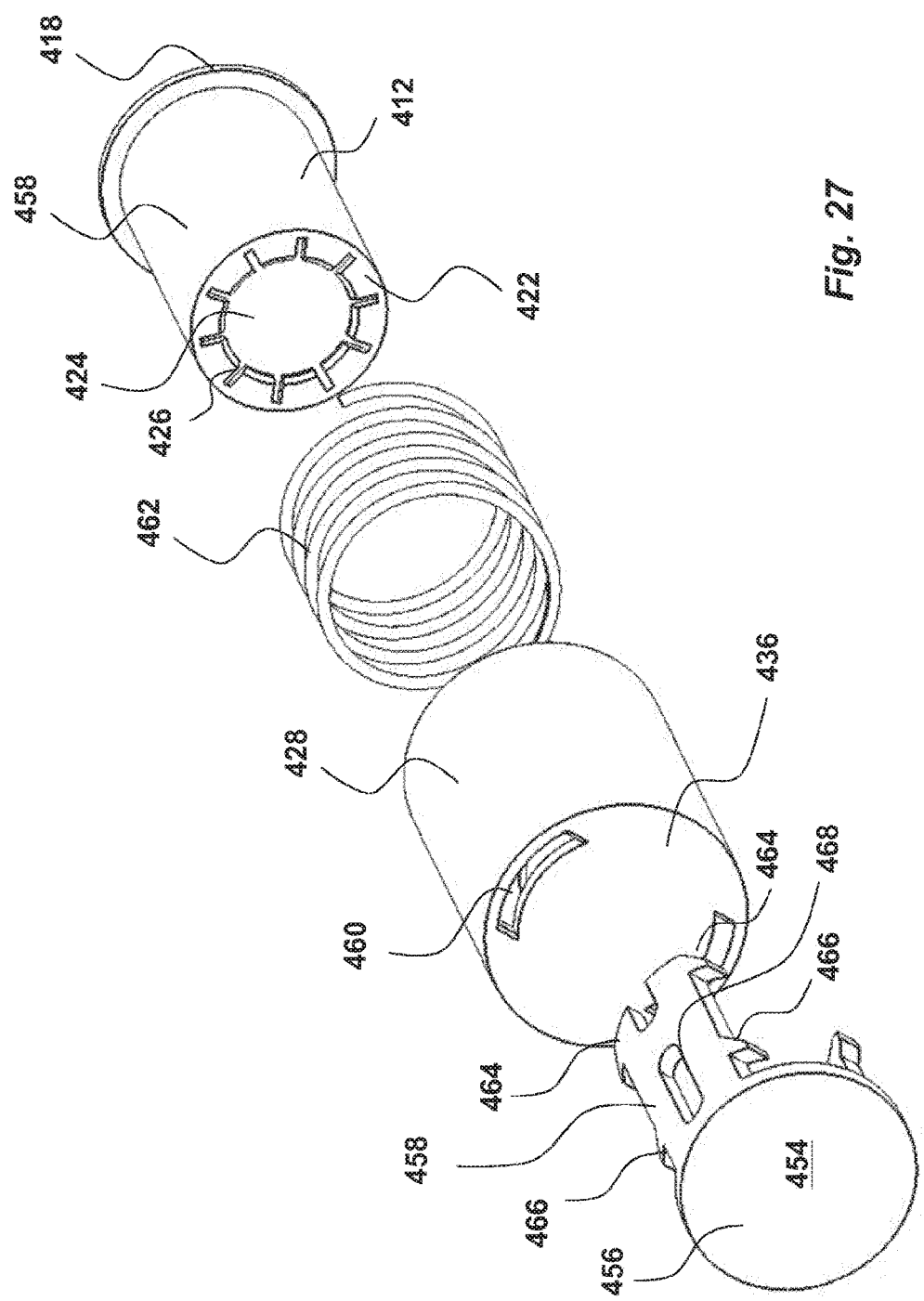
Figure 31:
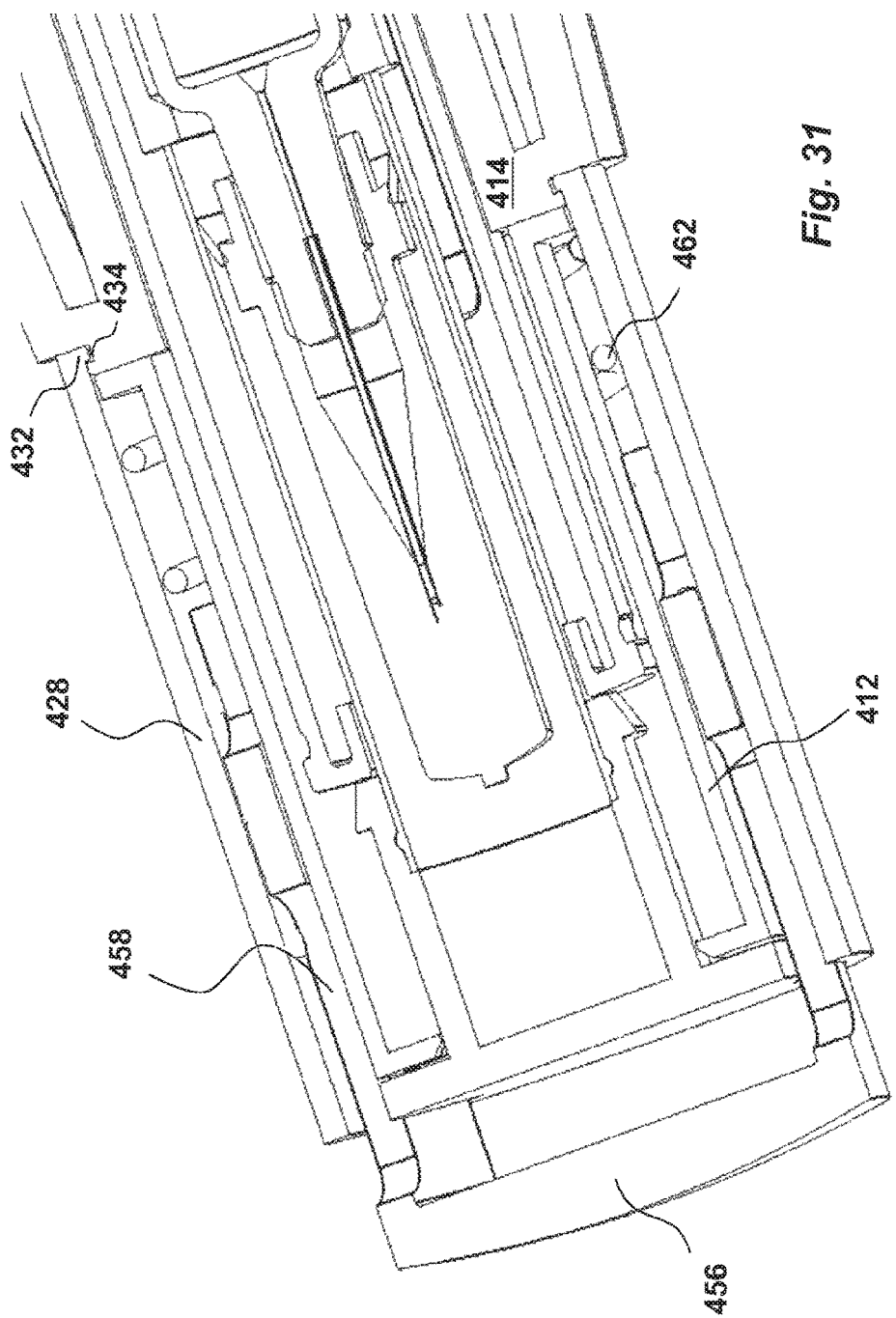

A generally tubular cap 428, FIGS. 26 and 27, is arranged radially outside, and coaxial with, the ejector sleeve 412. The inner diameter of the cap 428 is chosen generally the same as the outwardly directed distal ledge 418 of the ejector sleeve, thereby causing a circumferential gap 430, FIG. 28, between the ejector sleeve 412 and the cap 428. The cap 428 is arranged with inwardly directed protrusions 432 comprised in a second connecting means, FIGS. 29 and 31, at its distal end, which protrusions fit into a circumferential groove 434 comprised in a first connecting means; FIGS. 25 and 31, on a side surface of on the housing 414 adjacent the proximally directed surface 420 such that the cap 428 is releasably attached to the housing 414 of the medicament delivery device. An end wall 436, FIGS. 27 and 29, is further arranged in the proximal end of the cap 428, comprised in a second disconnecting means of the cap.

Figure 28:
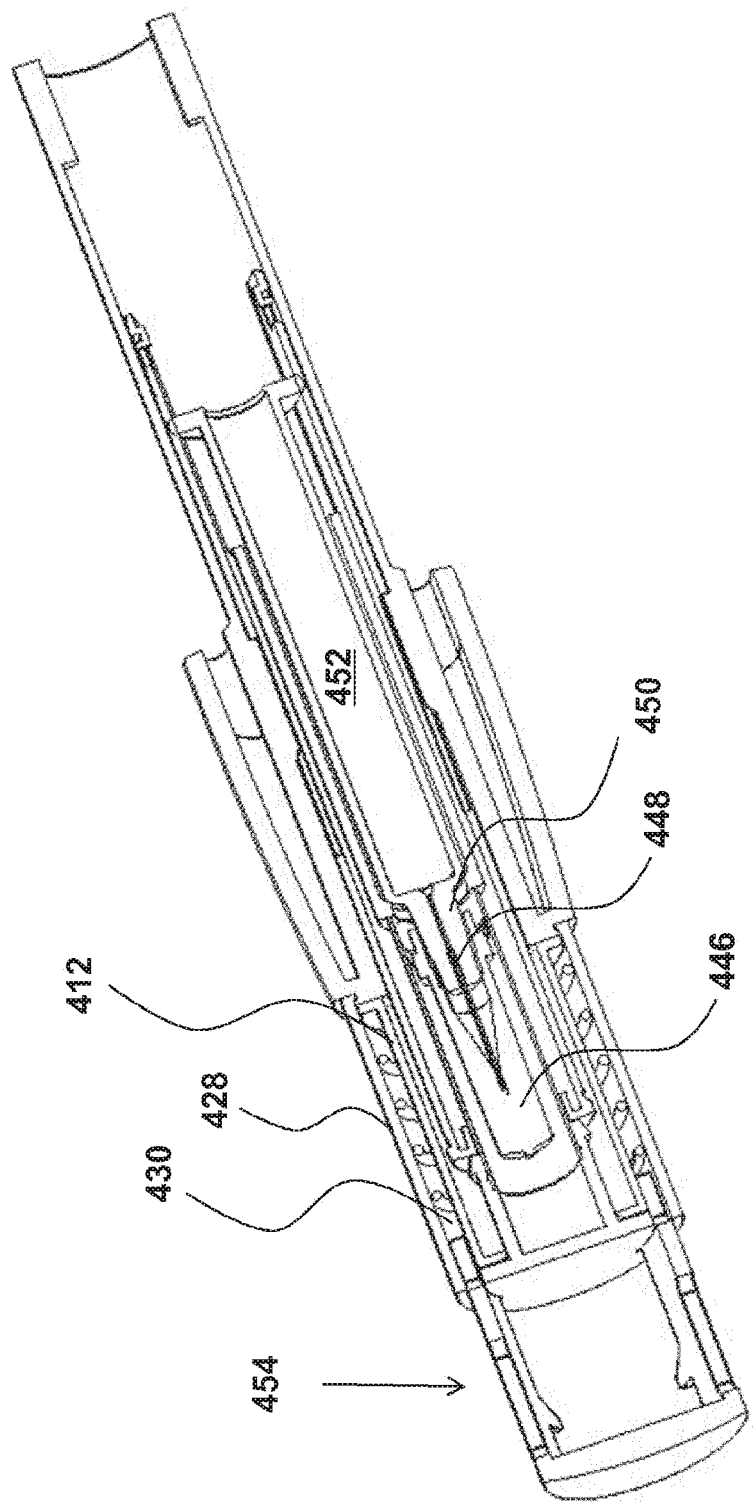
FIG. 28 is a cross-sectional view of the embodiment of FIG. 24, FIGS. 29-30 are detailed views of components comprised in the embodiment of FIG. 24, and FIGS. 31-35 are different detailed views of functional states of the embodiment of FIG. 24.
Figure 29:
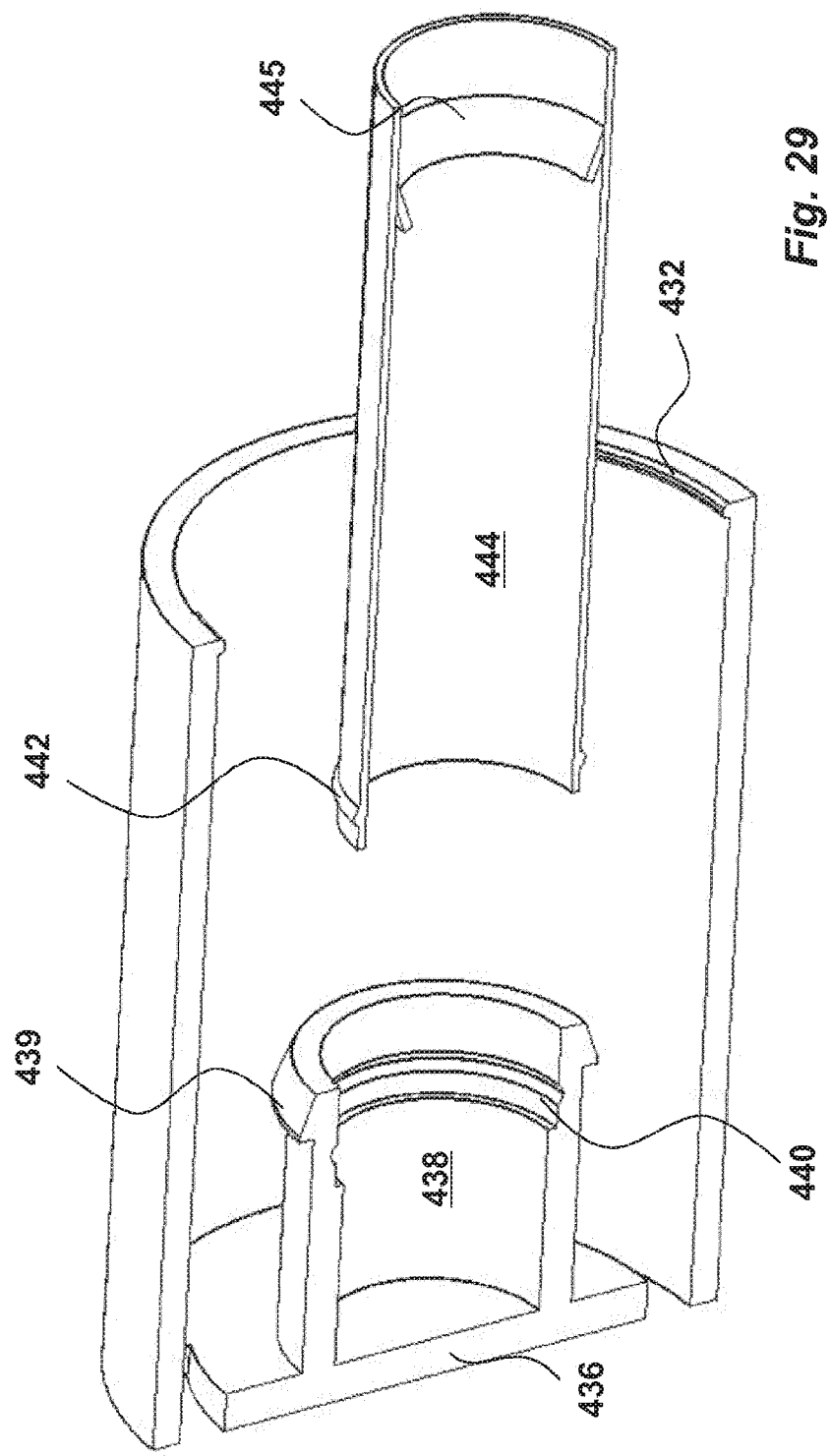

On an inner surface of the end wall 436, a generally tubular remover member 438, FIG. 29, is attached. The remover member 438 is arranged extending into the passage of the ejector sleeve 412. An inner surface of the tubular remover member 438 is arranged with a circumferential groove 440. A circumferential protrusion 442 arranged on an outer surface of a tubularly shaped needle shield remover 444 comprised in a third connecting means, FIG. 29, fits into the circumferential groove 440, thereby locking the needle shield remover 444 to the remover member 438. The needle shield remover 444 is further arranged with an inwardly inclined, proximally directed gripping member 445, which gripping member is intended to grip into the elastic material of a flexible needle shield 446, which needle shield 446 surrounds an injection needle 448 as well as a proximal neck portion 450 of a medicament container 452, FIG. 28. The remover member 438 is further arranged with a circumferential, outwardly extending ledge 439 at a distal end thereof, FIG. 29.

Figure 30:
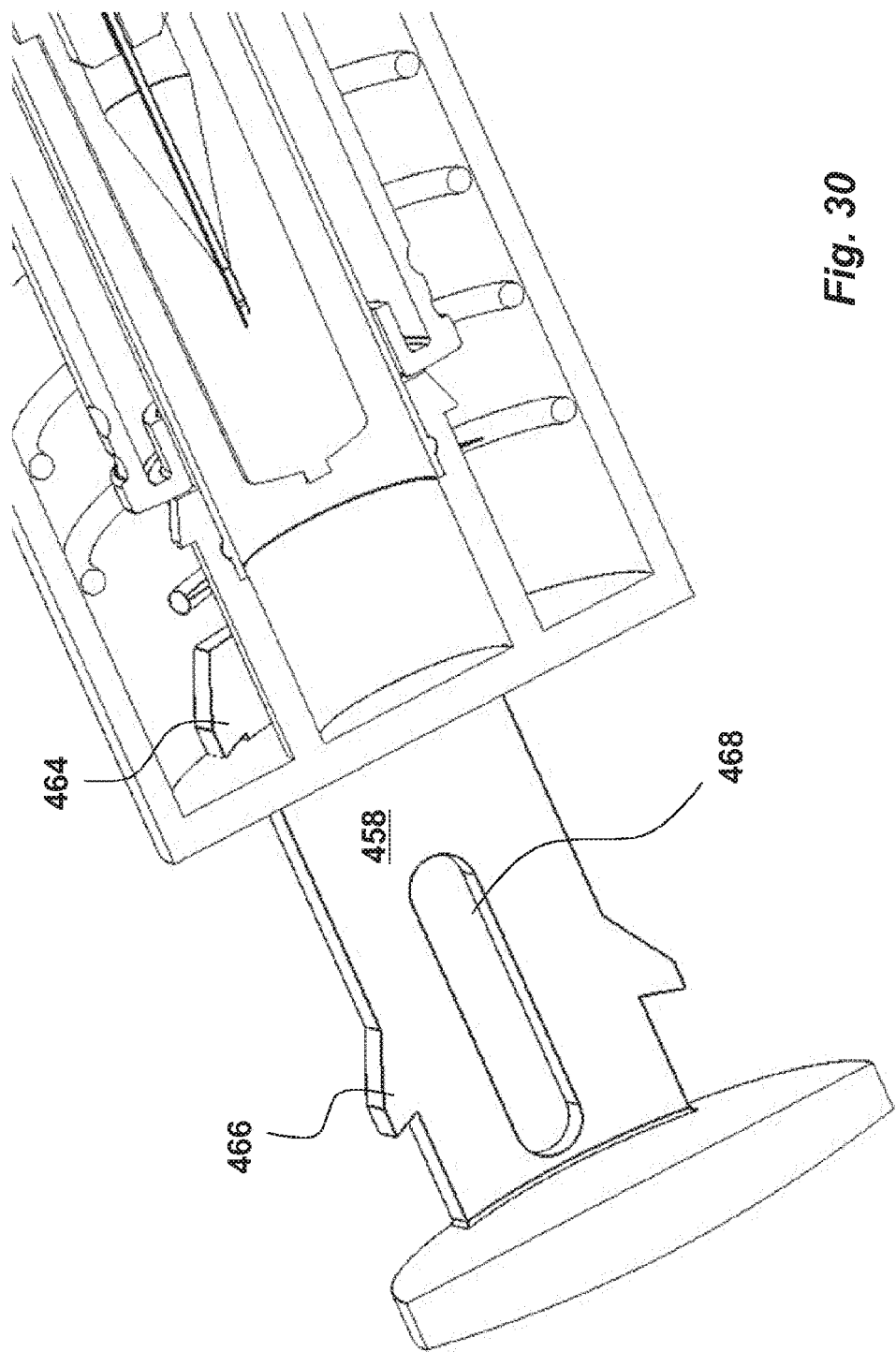

An activation member 454, FIG. 25, is arranged in the proximal end of the device. It comprises a generally disc-shaped contact member 456, FIG. 27, having a proximally directed contact surface. From the distal surface of the contact member 456, two arms 458, FIGS. 26 and 27, extend distally. The arms 458 have generally rectangular shape as seen in a cross-section. Each arm extends into passages 460, FIG. 26, formed in the end wall 436 of the cap 428, where the shape of the passages 460 generally correspond to the rectangular cross-sectional shape of the arms 458. The arms 458 further extend into the gap 430 between the ejector sleeve 412 and the cap 428. The activation member 454 is connected to an energy accumulating member 462, e.g. a spring, FIG. 25. Together they form a first disconnecting means. The spring is arranged between the outwardly extending ledge 418 of the ejector sleeve 412 and a distally directed end surface of the arms 458, urging the activation member 454 in the proximal direction. In an initial position, the activation member 454 is however locked from being moved in the proximal direction by a first set of ledges 464, FIG. 27, extending from side surfaces of the arms 458 and being in contact with a distal surface of the end wall 436 of the cap 428, FIG. 30.

The arms 458 are also arranged with locking members, e.g. a second set of ledges 466, extending from side surfaces of the arms 458. The ledges are generally wedge-shaped as seen in the figures, the function of which will be described below. The arms 458 are further arranged with cut-outs 468 positioned between each set of second ledges 466, as will also be described.

The device is intended to function as follows. It is intended to be attached to the housing 414 of a medicament delivery device with the inwardly extending protrusions 432 of the cap 428 fitting into the circumferential groove 434 of the housing 414. A medicament container 452 with an FNS 446 is fitted into the housing 414, FIG. 28. When the device is attached to the housing 414, the needle shield of the FNS 446 slides into the needle shield remover 444. In the initial position, as seen in FIG. 28, the activation member 454 extends from the cap 428 in the proximal direction, biased by the spring 462. The distal surface of the end wall 436 of the cap 428 is in contact with a proximal end surface of the ejector sleeve 412.

Figure 32:
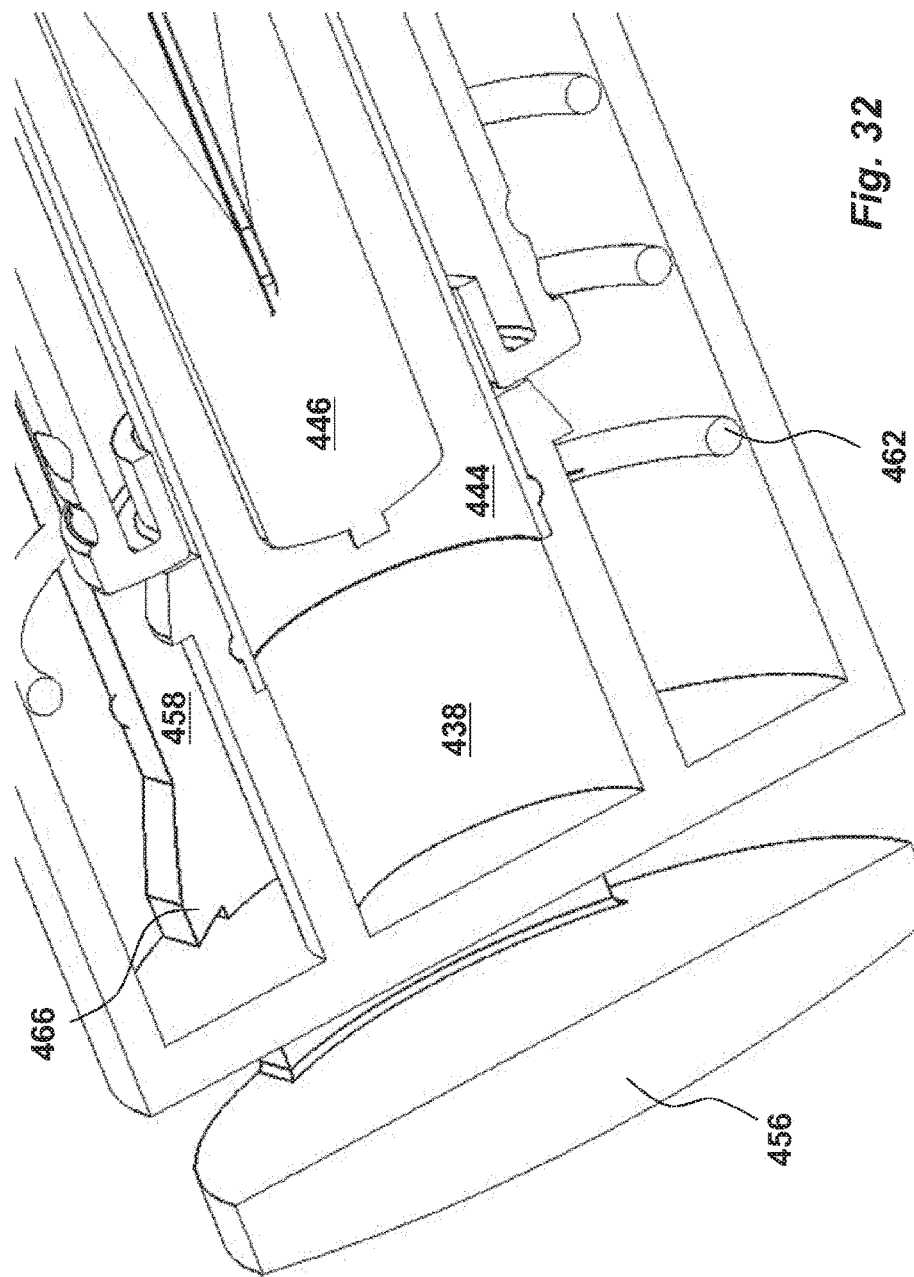

When the cap assembly is to be removed in order to use the medicament delivery device the user presses the activation member 454 at the proximal end of the device against a surface. The contact member 456 with the arms 458 will then be moved in the distal direction against the force of the spring 462. The arms 458 will move into the cap 428 and the second set of ledges 466 will pass the passages 460 of the cap. The passing of the second set of ledges 466 is facilitated by the wedge-shape of the ledges and the cut-outs 468 in the arms, where the latter enable a flexing transversal movement of the ledges 466. When the ledges 466 have passed the passages 460, the contact member 456 is locked from movement in the proximal direction relative to the cap 428 because the ledges 466 are locked by the distal surface of the end wall 436 of the cap 428, as seen in FIG. 32. The spring 462 has in turn been compressed by the movement of the contact member in the distal direction, building up a force in the spring 462, FIG. 31.

Figure 33:
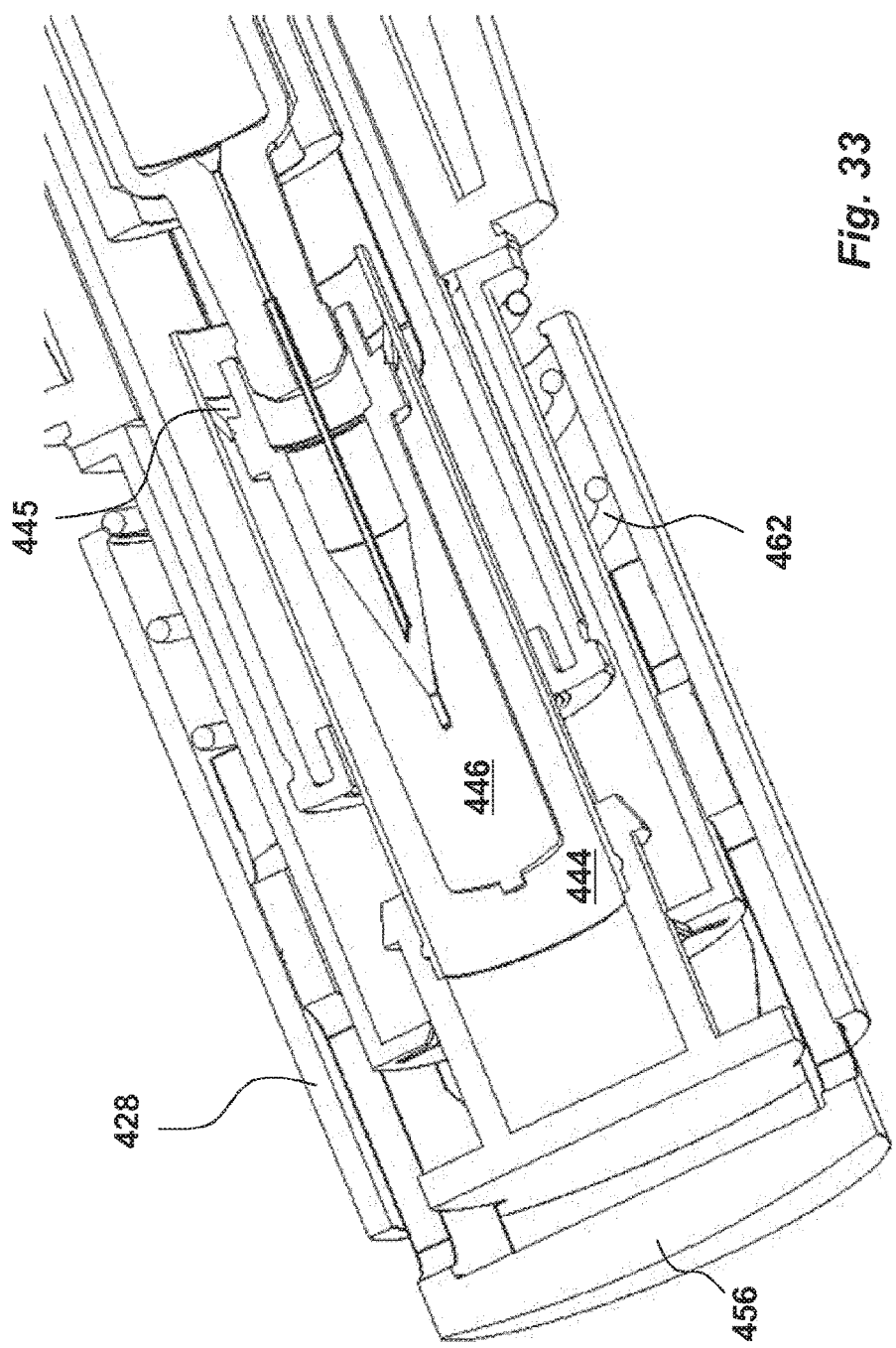

This force is now sufficient to overcome the holding forces between the protrusions 432 of the cap 428 and the groove 434 of the housing 414, whereby the cap 428 is moved in the proximal direction together with the contact member 456. The movement of the cap 428 also causes the needle shield remover 444, attached to the cap, to move in the proximal direction relative to the housing 414. The inclined gripping member 445 of the shield remover 444 will in turn grip into the flexible material of the FNS 446, whereby also the FNS 446 will be moved in the proximal direction, FIG. 33, relative to the injection needle 448. When the cap 428 has moved in the proximal direction a certain length, at a position where the FNS 446 is out of contact with the injection needle 448 and the proximal end of the medicament container, FIG. 34, the circumferential outwardly extending ledge 439 of the remover member 438, will come in contact with the inwardly directed ledge 422 of the ejector sleeve 412. Thus, the whole assembly is now removed, FIG. 35, and the medicament delivery device is ready for injection.

It is of course possible to remove the protective cap assembly 410 according to the fifth embodiment from the medicament delivery device purely manually without activating the automatic protective cap remover. The user may merely grip the protective cap and pull it in the proximal direction against the holding force between the protective cap and the housing and the friction between the injection needle and the shield.

It is to be understood that the embodiment described above and shown in the drawings is to be regarded only as a non-limiting example of the invention and that it may be modified in many ways within the scope of the patent claims.

The invention claimed is:

1. A medicament delivery device comprising:
a housing configured to receive a medicament container having a delivery member and a shield that covers said delivery member, the housing having a longitudinal axis, where the housing comprises a proximal end having a first connector;
a protective cap comprising a second connector configured to engage the first connector to secure the protective cap to the housing, wherein the first and the second connectors are configured such that an axial displacement of the protective cap relative to the housing disconnects the first and second connectors;
a shield remover connected and axially fixed to the protective cap, the shield remover comprising a gripping member configured to engage the shield when the protective cap is removed from the housing causing removal of the shield from the medicament container;
an actuator operably associated with the protective cap, where the actuator protrudes outwardly from an opening in the protective cap; and
a disconnection member is positioned within the protective cap and is directly connected to the protective cap, wherein movement of the actuator causes the disconnection member to exert an axial force on the protective cap to cause the protective cap and the shield to move in a proximal direction disconnecting the first connector from the second connector.

2. The medicament delivery device of claim 1 where the disconnection member comprises a spring operably connected to the housing, the protective cap and to the actuator such that the movement of the actuator causes the spring to be compressed and thereby to displace said protective cap.

3. The medicament delivery device of claim 1 wherein the first and second connectors are configured as a bayonet connection, a threaded connection, or protrusions and grooves.

4. The medicament delivery device of claim 1 where the delivery member comprises a needle, a nozzle or a mouth piece.

5. The medicament delivery device of claim 1 where the disconnection member comprises a nut operably connected to the housing and to the protective cap and drivably connected to a spring such that the movement of the actuator causes the nut to axially displace the protective cap.

6. The medicament delivery device of claim 5 where the nut has threads that are configured to cooperate and engage with corresponding threads on the housing.

7. The medicament delivery device of claim 5 where the nut has a bayonet connection member arranged to cooperate with a corresponding bayonet connection member on the housing.

8. The medicament delivery device of claim 1 where the disconnection member comprises a transmission comprising a rotator operably connected to the actuator to rotate the rotator.

9. The medicament delivery device of claim 8 where the rotator is arranged with first cam surfaces and protrusions, the transmission further comprises a guide member arranged with second cam surfaces such that rotation of the rotator by the actuator causes a displacement of the rotator in the proximal direction of the device.

10. The medicament delivery device of claim 1 where the delivery device is an injector, an auto-injector or inhaler.

* * * * *